(12) United States Patent
Tale et al.

(10) Patent No.: US 10,717,799 B2
(45) Date of Patent: Jul. 21, 2020

(54) COPOLYMERS AS EXCIPIENTS FOR EFFECTIVE SOLUBILIZATION OF POORLY WATER-SOLUBLE SUBSTANCES FROM SOLID MIXTURES

(71) Applicants: Dow Global Technologies LLC, Midland, MI (US); Rohm and Haas Company, Collegeville, PA (US); Regents of the University of Minnesota, Minneapolis, MN (US)

(72) Inventors: Swapnil Tale, Minneapolis, MN (US); Theresa M. Reineke, Vadnais Heights, MN (US); Frank S. Bates, Minneapolis, MN (US); Jeffrey M. Ting, Minneapolis, MN (US); Lakmini Widanapathirana, Minneapolis, MN (US); Steven J. Guillaudeu, Midland, MI (US); Li Guo, Humble, TX (US)

(73) Assignees: Dow Global Technologies LLC, Midland, MI (US); Rohm and Haas Company, Collegeville, PA (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/554,442

(22) PCT Filed: Feb. 24, 2016

(86) PCT No.: PCT/US2016/019342
§ 371 (c)(1),
(2) Date: Aug. 30, 2017

(87) PCT Pub. No.: WO2016/140845
PCT Pub. Date: Sep. 9, 2016

(65) Prior Publication Data
US 2018/0066091 A1    Mar. 8, 2018

Related U.S. Application Data

(60) Provisional application No. 62/127,874, filed on Mar. 4, 2015.

(51) Int. Cl.
*A61K 9/20*       (2006.01)
*C08F 220/56*    (2006.01)
(Continued)

(52) U.S. Cl.
CPC .......... *C08F 220/56* (2013.01); *A61K 9/1635* (2013.01); *A61K 9/2027* (2013.01); *C08F 220/54* (2013.01); *C08F 226/10* (2013.01)

(58) Field of Classification Search
CPC .... C08F 220/56; A61K 9/2027; A61K 9/1635
See application file for complete search history.

(56) References Cited

U.S. PATENT DOCUMENTS

2005/0158271 A1* 7/2005 Lee .................. A61K 9/145
                                                                    424/78.3
2005/0277739 A1* 12/2005 Yang ................ A61K 9/167
                                                                    525/242

(Continued)

FOREIGN PATENT DOCUMENTS

EP       1072617 A1    1/2001
WO     2005087825       9/2005

*Primary Examiner* — Michael L Leonard

(57) ABSTRACT

The present invention relates to the use of uncrosslinked copolymers having a backbone comprising i) a plurality of thermo-responsive structural units derived from one or more than one N-alkyl or N,N-dialkyl substituted (alkyl)acrylamide monomer and ii) a plurality of hydrophilic structural units derived from one or more than one second ethylenically unsaturated monomer as excipients in solid mixtures with poorly water-soluble substances for effective solubilization of the latter in aqueous media. Solid dosage forms comprising a solid mixture of such copolymer(s) and poorly (Continued)

water-soluble substance(s) are also within the scope of the invention.

17 Claims, 6 Drawing Sheets

(51) Int. Cl.
*A61K 9/16* (2006.01)
*C08F 226/10* (2006.01)
*C08F 220/54* (2006.01)

(56) References Cited

U.S. PATENT DOCUMENTS

| | | | |
|---|---|---|---|
| 2009/0053276 A1* | 2/2009 | Richard | A61K 9/0019 424/422 |
| 2012/0183500 A1* | 7/2012 | Rolfes Meyering | A61K 31/7088 424/93.1 |
| 2015/0374634 A1* | 12/2015 | Koo | C08L 53/00 424/451 |

* cited by examiner

COPOLYMERS AS EXCIPIENTS FOR EFFECTIVE SOLUBILIZATION OF POORLY WATER-SOLUBLE SUBSTANCES FROM SOLID MIXTURES

The present invention relates to the use of certain copolymers as excipients in solid mixtures with poorly water-soluble substances, particularly active pharmaceutical ingredients, for effective solubilization of these substances in aqueous media. Compositions comprising a solid mixture of such copolymer(s) and poorly water-soluble substance(s) as well as solid dosage forms containing these compositions are likewise within the scope of the invention.

INTRODUCTION

Many active substances like personal care active ingredients, food components, active pharmaceutical ingredients (APIs) or agrochemical agents have a lipophilic structure and are as such only poorly water-soluble, which may conflict with the intended use. For example, the majority of novel APIs suffers from poor solubility in aqueous media and concomitantly low bioavailability and efficacy, which frequently prevents their commercialization. Therefore different means and methods for effective solubilization and delivery of poorly water-soluble active substances in applications involving aqueous media have been devised. One approach commonly employed is based on combining the poorly water soluble substance with a suitable excipient. The excipient usually includes a surface-active compound comprising hydrophilic and lipophilic moieties, i.e. having an amphiphilic structure, capable of forming colloidal aggregates such as micelles in an aqueous environment. Lipophilic active substances can thus be transferred to and stabilized in the aqueous phase by incorporation into the lipophilic interior of such aggregates.

A broad variety of different substances have been investigated as excipients, e.g. oils, lipids, glycerides, fatty acids, fatty alcohols and derivatives such as polyalkoxylated derivatives of any of these, polymers such as polyethylene glycols, polypropylene glycols, polyethylene glycol methyl ethers, polyvinyl alcohols and polyoxyalkylene block copolymers, fatty acid esters of polyoxyethylene sorbitan, sodium lauryl sulphate, polyoxyethylene castor oil derivatives, vitamin E and derivatives thereof, and mixtures thereof to name just a few (cf. e.g. Handbook of Pharmaceutical Excipients, third Edition, edited by A. H. Kibbe, American Pharmaceutical Association and Pharmaceutical Press (2000)). However, most of the excipients known from the prior art have only modest to moderate effect in controlled release of lipophilic substances from solid formulations and stabilization of the released lipophilic substances in aqueous media.

In general, suitability of a compound as excipient in solid formulations, e.g. for oral drug delivery, requires not only effective and controlled release of the active substance from the solid to the liquid phase and stabilization of the released substance in aqueous media, but also that the compound is compatible with the other ingredients of the formulation and provides for a long term storage stability of the composition. The excipient should be able to inhibit phase changes such as a crystallization of the active ingredient in the solid formulation since frequently the active substance will originally be provided in the commonly better soluble amorphous form. Depending on the envisaged application further requirements such as e.g. physiological compatibility have to be fulfilled.

One of the most powerful excipients for solid pharmaceutical formulations, which mostly fulfils these requirements, is hydroxypropyl methyl cellulose acetate succinate (HPMCAS). However, HPMCAS, due to its ionic nature, may efficiently be used only in a limited pH range and fails to enhance the dissolution and/or to provide efficient stabilization of some lipophilic active substances such as several BCS class II drugs in aqueous media. Moreover, HPMCAS is a material of rather complex chemical composition, which renders systematic control of the material properties and preparation comparatively sophisticated.

Consequently there remains a need for alternative excipients suitable for the use in solid formulations, which enable controlled release and efficient solubilization of various poorly water-soluble active substances in aqueous media of a wide range of pH.

Homopolymers of N-isopropylacrylamide (NIPAM) and related monomers of the N-alkylated (alkyl)acrylamide type are well-known for their thermoresponsive behaviour showing a reversible coil-to-globule transition by hydration or dehydration, respectively, at the lower critical solution temperature (LCST). By copolymerization with suitable hydrophilic or hydrophobic monomers the LCST can be tuned and amphiphilic copolymers be obtained, which may reversibly self-assemble into micelles upon variation of the environmental temperature. For example, B. Liu et al. describe in Journal of Polymer Science, vol. 43, 3643-3654 (2005) smart amphiphilic block copolymers with a switchable hydrophilic-hydrophobic block of poly-NIPAM and a hydrophilic block of poly(N-dimethylacrylamide).

Micellar solutions of such thermoresponsive copolymers have been prepared and loaded with drugs for use of the micellar solutions as drug delivery vehicle. However, the use of such copolymers as excipient for the solubilization and controlled release of poorly water-soluble substances from solid mixtures has not been described so far. The dissolution process of a solid formulation differs fundamentally from the release of a substance loaded to micelles in solution. The solid body gradually disintegrates by phase transfer processes at the solid/liquid interface. The excipient generally assists in the transfer of poorly soluble substances from the solid to the liquid phase and stabilization versus re-precipitation, wherein the excipient itself dissolves or becomes dispersed in the liquid phase. Release of substances from micelles in solution rather involves a re-distribution in a stabilized liquid colloidal system and no disintegration of a bulk solid body.

Besides micellar solutions also copolymer hydrogels of the above-mentioned thermoresponsive copolymers have been proposed for drug delivery (cf. e.g. R. Yoshida et al., Journal of Biomaterials Science, Polymer Edition, 6 (6), 585-598 (1994)). Such hydrogels differ from excipients in the usual sense in that the hydrogel copolymer is insoluble in the liquid phase and forms a matrix, wherefrom incorporated substances can be released by reversible swelling of the gel in response to the temperature. Such hydrogels are obtainable by including a cross-linker such as a diethylenically unsaturated compound in the preparation of the thermoresponsive copolymer for the formation of a cross-linked network.

In view of the foregoing, the present invention aims to provide alternative compounds for the use as excipients in solid formulations, which ideally enable a controlled rapid release and more efficient solubilization of various poorly water soluble substances in different aqueous media of a wide pH range, effectively inhibit crystallization, provide long-term stable formulations, are physiologically compatible and can be prepared cost-efficiently from readily available resources. It is a further objective of the present invention to provide corresponding formulations comprising such enhanced excipient(s) in solid mixture with poorly water soluble substance(s) in dosage forms with high users' acceptance.

SUMMARY

In a first aspect, the present invention thus relates to a composition comprising a solid mixture comprising:
a) at least one uncrosslinked copolymer having a backbone comprising i) a plurality of thermo-responsive structural units derived from one or more than one first monomer, which is an N-alkyl or N,N-dialkyl substituted (alkyl) acrylamide monomer, and ii) a plurality of hydrophilic structural units derived from one or more than one second monomer, which is an ethylenically unsaturated monomer, and
b) at least one poorly water soluble substance.

In another aspect, the present invention is directed towards solid dosage forms comprising the afore-mentioned composition.

The present invention is also related to the use of the copolymer as defined above in the context of the composition according to the present invention to increase the solubility and/or the dissolution rate of a poorly water soluble substance in an aqueous medium and/or to inhibit crystallization of a poorly water soluble substance and/or to increase the bioavailability of a poorly water soluble substance.

The present invention is based on the unexpected finding that uncrosslinked polymers derived from copolymerization of one or more than one type of N-alkyl or N,N-dialkyl substituted (alkyl)acrylamide monomer(s) providing thermo-responsiveness and one or more than one type of ethylenically unsaturated monomer(s) providing hydrophilic properties may drastically increase the solubility of various poorly water-soluble drugs in aqueous media and enable to maintain a highly supersaturated state over substantial periods of time, e.g. 6 hours or more. These copolymers are able to form homogeneous solid dispersions with poorly water soluble substances, which are long term stable under typical storage conditions and exhibit rapid dissolution characteristics. Herein, the copolymers are capable of effectively stabilizing the poorly water soluble substance(s) in amorphous form thus inhibiting crystallization in the solid mixture. Said copolymers are moreover non-toxic, physiologically compatible and can be prepared in a cost-efficient manner from readily available resources using established polymerization techniques. These characteristics render the afore-mentioned copolymers particularly suitable as excipient in solid mixtures with poorly water soluble substances such as in particular APIs achieving comparable or even enhanced dissolution and solubilization characteristics compared to state of the art excipients such as HPMCAS. The typically non-ionic nature of said copolymers is moreover envisaged to enable efficient use as excipient in a wider pH range than HPMCAS. Thus the afore-mentioned copolymers, which are described in more detail below, help to release poorly water-soluble substance(s) from solid compositions in sufficient dosage for applications, wherein a concentration level of the poorly water-soluble substance(s) in aqueous media well above its inherent solubility limit is desired/required, e.g. for enhancing the bioavailability of an API and/or for achieving a certain (e.g. therapeutic or physiological) effect.

DESCRIPTION OF EMBODIMENTS

Figure 1:
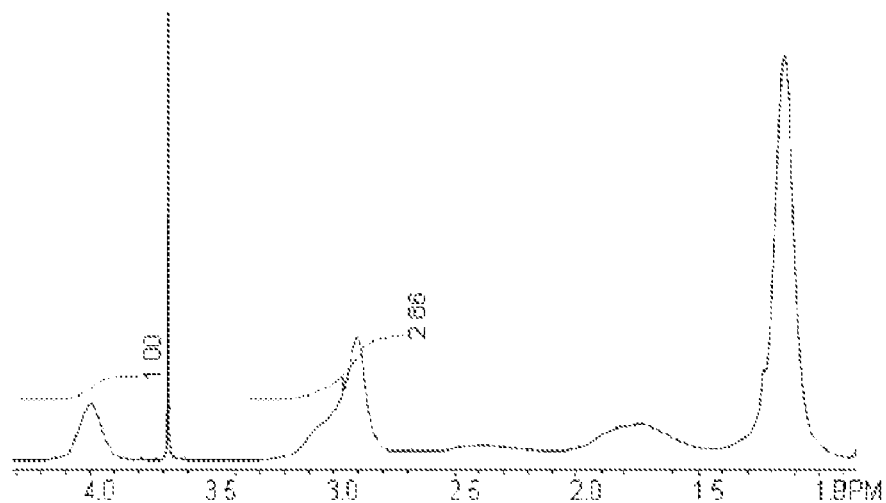
FIG. 1 shows the $^1$H-NMR spectrum (500 MHz, CDCl$_3$) of a NIPAM-co-DMA polymer (polymer of Example 1-6) having a backbone constituted of about 66 mol % structural units derived from NIPAM and about 34 mol % structural units derived from DMA as calculated from the ratio of the indicated relative integrated peak areas according to the procedure outlined in the Examples.

As pointed out above, the nature of the copolymer used as component a) in the solid mixture of the compositions according to the present invention is a key aspect of the present invention. According to the present invention the copolymer is an uncrosslinked copolymer having a backbone comprising
(i) a plurality of thermo-responsive structural units derived from one or more than one first monomer, which is an N-alkyl or N,N-dialkyl substituted (alkyl)acrylamide monomer, and
(ii) a plurality of hydrophilic structural units derived from one or more than one second monomer, which is an ethylenically unsaturated monomer.

In the context of the present invention the term "uncrosslinked" means that the copolymer comprises a plurality of discrete molecules, which are not covalently bound to each other. The copolymer molecules may e.g. have a linear structure or have a linear main chain with attached side chains, but typically not highly branched structures or three dimensional networks. Thus "uncrosslinked" may in particular mean that no crosslinking agent such as a polyunsaturated compound is used in the preparation of the copolymer. Crosslinking is generally not desirable in the present case as it degrades the solubility of the copolymer and impedes or prevents disintegration of a solid mixture comprising the copolymer in aqueous media, which is considered important for efficient use as excipient, and rather leads to insoluble, swellable gels. Preferably the copolymer according to the present invention is a linear copolymer.

The term "backbone" refers within the context of the present invention to the main chain in the molecular structure of the copolymer. The main chain can be identified as the series of covalently bound structural units derived from the monomers used in the copolymerization, which together form the continuous chain (of maximum length) of the copolymer molecule. Optionally, the copolymer according to the present invention may comprise side chains or grafted chains pendant to the backbone.

By structural unit derived from monomer X and the like it is referred in the context of the present invention to the smallest repetition unit in the polymer structure that is formed from monomer X. When the copolymer is formed by the generation of covalent bonds between initially unsaturated monomers as e.g. in an addition polymerization reaction of ethylenically unsaturated monomers, the structural unit derived from a certain unsaturated monomer corresponds structurally to the monomer except for the degree of unsaturation. In case of a monoethylenically unsaturated monomer such as N-alkyl or N,N-dialkyl substituted (alkyl)acrylamide the structural unit derived from the monoethylenically unsaturated monomer can e.g. be conceptualized as a divalent ethylenically saturated radical of the monomer. The polymer chain is then formally generated by coupling a plurality of structural units derived from their corresponding monomers forming covalent bonds between adjacent structural units via the conceptualized radical sites.

As mentioned above, the copolymer used according to the present invention comprises a plurality of thermo-responsive structural units derived from one or more than one first monomer. Herein, thermo-responsiveness means that the structural units derived from the first monomer are capable of undergoing a substantial change in their conformation, hydrophilicity and/or hydration in response to a change in temperature. In particular they may exhibit a reversible change in any one of these properties around a certain temperature. Accordingly, the dissolution/dispersion characteristics of the copolymer may be temperature-dependent. In particular the copolymer may exhibit a change from a state of comparatively high solubility/dispersibility in aqueous media (the copolymer being e.g. molecularly dissolved or colloidally dispersed) to a state, wherein the solubility in aqueous media is significantly lower (copolymer e.g. forming larger aggregates) above a temperature commonly referred to as the lower critical solution temperature (LCST). The LCST may e.g. be determined by monitoring changes in the optical properties of a solution of a copolymer comprising thermo-responsive structural units in an aqueous medium of interest as a function of the solution temperature, such as by temperature-dependent transmittance or turbidity measurements e.g. as outlined in the Examples.

The one or more than one first monomer, i.e. the type of monomer providing thermo-responsive structural units to the copolymer, is generally an N-alkyl or N,N-dialkyl substituted (alkyl)acrylamide monomer. In the context of the present invention the notation "(alkyl)acrylamide" means that it is jointly referred to acrylamide and alkylacrylamides such as e.g. methacrylamides, ethacrylamides etc. Analogously the term "(alkyl)acrylic acid, "(alkyl)acrylate" and the like shall be construed to refer herein to unsubstituted acrylic acid or acrylates, respectively, and the alkylated derivatives thereof. Likewise e.g. the term "(meth)acrylamide" shall be construed to refer to acrylamide and methacrylamide moieties, the term "(meth)acrylate" to encompass acrylates and methacrylates and so forth.

According to the present invention the term "alkyl" shall be construed in its broadest sense to encompass unsubstituted alkyl moieties, i.e. moieties of the composition $C_nH_{2n+1}$ (n: integer $\geq 1$) and $C_nH_{2n-1}$ (cyclic structure; n: integer $\geq 1$), as well as alkyl and cycloalkyl moities, wherein one or more than one hydrogen atom(s) is substituted by a functional group such as hydroxyl, carboxy, amine, thiol or halogen and/or wherein one or more than one heteroatom, i.e. atom other than C and H, is comprised. Preferably the term alkyl refers to unsubstituted $C_nH_{2n+1}$ moieties though, which can e.g. be linear or branched.

According to the present invention in principle any N-alkyl or N,N-dialkyl substituted (alkyl)acrylamide, which imparts thermo-responsive structural units, could be used as first monomer for preparation of the copolymer of the present invention. Non-limiting examples of N-alkyl or N,N-dialkyl substituted (alkyl)acrylamide monomers, which can be used as first monomer, comprise e.g. N-isopropyl (meth)acrylamide, N,N-diethyl(meth)acrylamide, N-tert-butyl(meth)acrylamide, N-hydroxypropyl(meth)acrylamide, N-piperidyl (meth)acrylamide and combinations thereof. Preferably the first monomer comprises N-isopropylacrylamide. The copolymer according to the present invention may comprise thermo-responsive structural units derived from a single type of the first monomer or derived from a combination of different types of the first monomer. Preferably the copolymer comprises thermo-responsive structural units derived from a single type of the first monomer, preferably N-isopropylacrylamide.

As mentioned above, the copolymers according to the present invention comprise furthermore a plurality of hydrophilic structural units derived from one or more than one second monomer in the polymer backbone. Hydrophilic structural units are structural units that have an affinity to water. In the context of the present invention, this can mean in particular that incorporation of structural units derived from the second monomer increases the solubility and/or the LCST of the polymer in water or an aqueous medium compared to the corresponding polymer obtained by polymerization of the one or more than one first monomer only.

The second monomer is an ethylenically unsaturated monomer. In principle any kind of ethylenically unsaturated monomer that provides hydrophilic properties in the afore-mentioned sense to the copolymer according to the present invention can be employed. In contrast to the one or more than one first monomer, the one or more than one second monomer typically does not impart thermo-responsive characteristics to the copolymer, in other words the conformation, hydrophilicity and/or hydration of the structural units derived from the second monomer do not change substantially with variation of the temperature in the relevant temperature range for liquid aqueous media, i.e. between the freezing and boiling point such as between 0° C. and 100° C. Typically the second monomer is monoethylenically unsaturated, i.e. comprises a single C=C bond. The one or more than one second monomer may e.g. comprise an ethylenically unsaturated amide, amine, carboxylic acid, carboxylate, hydroxylamine, glycol or alcohol and combinations thereof. Herein the term glycol comprises monomeric diols such as ethane-1,2-diol, propane-1,2-diol, propane-1,3-diol or 2,2-dimethyl-1,3-propanediol and oligomeric and polymeric diols obtainable by condensation of monomeric diols like 2-(2-hydroxyethoxy)ethan-1-ol, 2-[2-(2-hydroxyethoxy)ethoxy]ethanol, polyethylene oxide, polypropylene oxide and mixed polyalkylene oxides as well as derivatives of any of these, wherein one or both of the alcoholic hydroxyl groups is/are etherified (e.g. OH group replaced by a methoxy group) or esterified, in particular with an unsaturated carboxylic acid like an (alkyl)acrylic acid such as (meth)acrylic acid. Non-limiting examples of suitable ethylenically unsaturated glycols are (meth)acrylates of any one of the diols or etherified derivatives mentioned above such as ethylene glycol (meth)acrylate, ethylene glycol methyl ether (meth)acrylate, polyethylene glycol meth (acrylate) and polyethylene glycol methyl ether meth(acrylate).

The one or more than one second monomer may in particular be selected from (alkyl)acrylic acid, (alkyl)acrylates, (alkyl)acrylamides, substituted derivatives thereof and combinations of any of the afore-mentioned compounds. Accordingly, the one or more than one second monomer can e.g. comprise one or more than one compound having a structure according to any one of the following formulas (I) and (II):

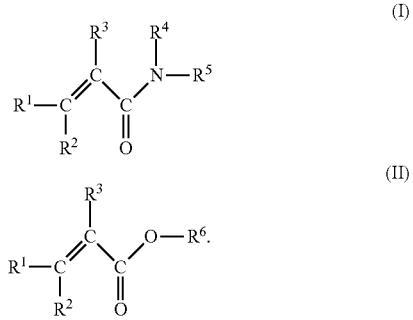

Herein, each of $R^1$, $R^2$, $R^3$, $R^4$ and $R^5$ is independently selected from hydrogen and a monovalent organic group having from 1 to 6 carbon atoms. Suitable monovalent organic groups can in particular be exemplified by linear or branched alkyl groups. Non-limiting examples are e.g. methyl, ethyl, n-propyl, isopropyl, n-butyl, sec-butyl, tert-butyl, pentyl and hexyl. $R^6$ may be as defined for $R^1$ to $R^5$ or may be a moiety derived (by esterification) from a glycol such as e.g. ethane-1,2-diol, propane-1,2-diol, oligomers and polymers of ethylene oxide and/or propylene oxide and etherified (e.g. methoxylated) derivatives of any one of the foregoing. Preferably, $R^1$ and $R^2$ are hydrogen, $R^3$ is selected from hydrogen and a methyl group, and $R^4$, $R^5$ and $R^6$ are each independently selected from hydrogen and an alkyl group having from 1 to 4 carbon atoms.

Furthermore e.g. also vinyl-substituted heterocyclic compounds such as 4-vinyl-pyrrolidone can be employed as second monomer for introducing hydrophilic structural units to the copolymer. Preferably the one or more than one second monomer is selected from the group consisting of N,N-dimethylacrylamide, acrylamide, acrylic acid, 2-hydroxyethyl-methacrylate, N-(hydroxymethyl)acrylamide, 4-vinyl-pyrrolidone and combinations thereof.

The copolymer according to the present invention may comprise hydrophilic structural units derived from a single type of the second monomer or derived from a combination of different types of the second monomer. Preferably the copolymer comprises hydrophilic structural units derived from a single type of the second monomer such as N,N-dimethylacrylamide.

The molar ratio of the thermo-responsive structural units i) to the hydrophilic structural units ii) comprised in the copolymer is generally not limited, but is preferably in a range from 1:1 to 10:1, preferably from 1.2:1 to 5:1, more preferably from 3:2 to 4:1.

In addition to the thermo-responsive structural units and the hydrophilic structural units derived from the afore-mentioned first and second monomers, respectively, the copolymers according to the present invention may optionally include further structural units derived from other monomers. In principle any kind of unsaturated, e.g. ethylenically unsaturated, monomer can be copolymerized with the first and second monomers to introduce structural units of a desired functionality as long as these additional structural units do not interfere with the use of the copolymers as excipient in solid mixtures for solubilization of poorly water soluble substances and/or degrade the copolymer properties such as stability, solubilizing capabilities and compatibility with other ingredients. For instance the copolymer may comprise hydrophobic structural units derived from one or more than one type of lipophilic monomers. Hydrophobic structural units are structural units that have an affinity to non-polar media and thus dislike water. In the context of the present invention, this can mean in particular that incorporation of structural units derived from lipophilic monomers decreases the solubility and/or the LCST of the copolymer in water or an aqueous medium compared to the polymer obtained by polymerization of the one or more than one first monomer only. Suitable non-limiting lipophilic monomers that can be used to incorporate hydrophobic structural units to the copolymer are for example unsaturated fatty acids, (meth)acrylates of lipophilic hydroxyl-functional compounds like fatty alcohols such as $C_8$-$C_{30}$ alkanols, or unsaturated hydrocarbons such as styrene, propylene and ethylene.

Nevertheless, the copolymer according to the present invention comprises typically predominantly or exclusively thermo-responsive structural units i) and hydrophilic structural units ii) such as more than 70 mol %, preferably more than 80 mol %, more preferably at least 90 mol % or at least 95 mol % or 100 mol %, based on the total amount of monomer-derived structural units constituting the copolymer. Optional other monomer-derived structural units typically are comprised in the copolymer, if present at all, in an amount of less than 30 mol %, preferably less than 20 mol %, more preferably not more than 10 mol % or not more than 5 mol % or 0 mol %, based on the total amount of monomer-derived structural units constituting the copolymer. Preferably the copolymer according to the present invention comprises from greater than 50 mol % to less than or equal to 90 mol %, preferably from 55 mol % to 80 mol %, more preferably from 60 to 75 mol %, of the thermo-responsive structural units i) and/or from equal to or greater than 10 mol % to less than 50 mol %, preferably from 20 mol % to 45 mol %, more preferably from 25 mol % to 40 mol % of the hydrophilic structural units ii), based on the total amount of monomer-derived structural units constituting the copolymer. Preferably the amounts of the thermo-responsive structural units i) and the hydrophilic structural units ii) sum up herein to 100 mol %. Copolymers of such compositions have been found to be particularly effective in solubilizing poorly water-soluble substances in aqueous media and maintaining a highly supersaturated state over extended periods of time.

The molar composition of the copolymer may systematically be controlled in a straightforward manner by adjusting the relative amounts of the monomers in the reaction mixture used to prepare the copolymer. The molar composition of the copolymer can be readily determined e.g. by nuclear magnetic resonance (NMR) spectrometric analysis through identification of the characteristic signals of the different constituting structural groups and comparison of the respective relative integrated peak areas taking into account the number of nuclei per structural unit responsible for the different signals, for instance according to the procedure outlined in the Examples.

Typically the copolymer according to the present invention is a binary copolymer, i.e. obtained by copolymerizing one type of the first monomer set forth above providing the thermo-responsive structural units (i) and one type of the second monomer as set forth above providing the hydrophilic structural units (ii). Suitable binary copolymers are e.g. poly-[(N-isopropylacrylamide)-co-(N,N-dimethylacrylamide)], poly-[(N-isopropylacrylamide)-co-(acrylamide)], poly-[(N-isopropylacrylamide)-co-(4-vinyl-pyrrolidone)], poly-[(N,N-diethylacrylamide)-co-(N,N-dimethylacrylamide)] and poly-[(N-isopropylacrylamide)-co-(2-hydroxy-ethyl-methacrylate)]. Particularly preferred is poly-[(N-isopropylacrylamide)-co-(N,N-dimethylacrylamide)].

The distinct structural units constituting the copolymer according to the present invention can generally be arranged randomly or blockwise in the copolymer. Random arrangement includes structures wherein the distinct types of constituting structural units are distributed statistically in a homogeneous manner over the copolymer chains as well as chain structures comprising different types of structural units wherein at least one type of structural unit is preferentially bound to structural units of either the same type or a distinct type. In contrast thereto, upon blockwise arrangement constituting structural units of the same type each form one or more substructures of considerable length in proportion to the total copolymer chain, a substructure (block) making up for instance at least 5 mol %, or at least 10 mol %, or at least 20 mol %, or at least 30 mol % of the total amount of monomer-derived structural units constituting the copolymer. For example all thermo-responsive structural units present in a copolymer molecule may be connected in series to form a thermo-responsive block and all hydrophilic structural units may be connected in series to form a hydrophilic block. The thermo-responsive block and the hydrophilic block can then be coupled to one another forming a diblock copolymer. Alternatively, two or more blocks made entirely of structural units of the same type such as e.g. thermo-responsive structural units, hydrophilic structural units, or hydrophobic structural units, if present, can be present in the copolymer molecules. Preferably, the copolymers according to the present invention are random copolymers though.

As the skilled artisan is aware of, a polymeric material in general consists of a plurality of individual macromolecules, which may differ in the number and distribution of the constituent structural units. Therefore, it is common to describe the polymer properties, as also done throughout this specification, if not specified to the contrary, by average values for the entity of macromolecules constituting the polymer. In particular, the copolymer of the present invention thus exhibits generally a distribution of macromolecules of different molecular weight. The molecular weight distribution may be measured e.g. by size exclusion chromatography and the number average molecular weight ($M_n$) and the weight average molecular weight ($M_w$) be deduced from these data. The copolymer according to the present invention typically has a number average molecular weight in the range from 3,000 to 400,000 g/mol, preferably from 5,000 to 200,000 g/mol, more preferably from 10,000 to 120,000 g/mol or from 10,000 to 80,000 g/mol, and/or has a polydispersity index (PDI=$M_w/M_n$) of less than 2.5, preferably less than 2.0 or less than 1.5, more preferably less than 1.3 or equal to or less than 1.2 or equal to or less than 1.1, as determined each by size exclusion chromatography using light scattering e.g. according to the procedure outlined in the Examples.

The copolymers according to the present invention are furthermore preferably non-ionic. Herein, the term "non-ionic" means that the copolymer comprises no ionic groups or groups which readily form ions in aqueous medium such as by heterolytic dissociation of one or more covalent bonds or by binding of protons or Lewis acids. The presence of ionic groups such as carboxylate groups and acid or basic groups typically renders the solubility and solubilizing properties of the copolymer markedly pH-dependent. Non-ionic copolymers are on the other hand considered to advantageously exhibit solubility and solubilizing properties, which depend less on the pH value, and thus may enable use in a wider pH range.

The copolymers according to the present invention generally exhibit thermo-responsive properties. Typically they exhibit a LCST in water or aqueous medium greater, such as at least 2 K greater or at least 5 K greater or at least 10 K or at least 15 K or at least 25 K greater, than the LCST of the corresponding polymer obtained by polymerization of the one or more than one first monomer only. The LCST measured for a 1 wt. % solution of the copolymer in deionized water or in phosphate buffer saline by determination of the cloud point or the sudden change in optical transmission by temperature-dependent optical measurements as outlined in the Examples can for instance be 30° C. or more, or 35° C. or more, or 40° or more, or 50° C. or more, for binary copolymers comprising thermo-responsive structural units derived from NIPAM.

The copolymers according to the present invention can be prepared from the afore-mentioned monomers in a cost-efficient manner by established addition polymerization techniques known as such from the prior art, see e.g. G. Odian, principles of polymerization, 3$^{rd}$ ed., John Wiley & Sons. The chain growth may proceed via radical or ionic active species or intermediates formed with metal organic catalysts. In particular the copolymers according to the present invention can be formed by radical polymerization. Herein, radical species are generated in the reaction mixture comprising the monomers and stepwise add monomer units. Chain propagation proceeds until termination e.g. by a radical transfer or recombination reaction occurs or the monomers have been consumed. The initiating radicals can e.g. be generated by heating the reaction mixture, exposing it to electromagnetic radiation and/or ionizing particles such as microwaves, infrared radiation, UV radiation, X-rays or γ-rays, electrons, plasma or α-radiation and/or by including one or more than one initiator in the reaction mixture. Non-limiting examples of suitable initiators are e.g. peroxides such as di-tert-butyl peroxide, dibenzoyl peroxide, methyl ethyl ketone peroxide, peroxydisulfate salts (e.g. potassium peroxydisulfate), hydroperoxides such as cumene hydroperoxide and azo compounds such as azobisisobutyronitrile (AIBN). Optionally the reaction mixture may further comprise one or more than one chain transfer agent (CTA) for controlling the molecular weight and its distribution. Non-limiting examples of chain transfer agents, which may be useful in preparing the copolymers according to the present invention are thiols such as dodecylmercaptan, tert-butyl mercaptan, tert-nonyl mercaptan, pentaerythritol tetrakis(3-mercaptopropionate) or 4,4'-thiobenzenethiol, halocarbons such as bromotrichloromethane and tetrachloromethane and thiocarbonylthio compounds such as dithioesters, trithiocarbonates, thiocarbamates and xanthates. The polymerization can be carried out in bulk, in solution, in dispersion or as an emulsion polymerization. The chemical composition of the copolymer in terms of the molar proportions of the constituting structural units and their distribution along the polymer chain can be controlled by adjusting the relative amounts of the monomers used for the preparation in the reaction mixture. Herein, the monomers may be provided to the reaction mixture as one batch or may be incrementally or continuously supplied. Random copolymers may e.g. be obtained when the monomers are polymerized from a batch. Block copolymers may e.g. be obtained by stepwise subsequent polymerization of different monomers. For instance a diblock copolymer may be prepared by polymerizing in a first step one or more than one first monomer of the above-described kind to obtain thereby macroradicals comprising a plurality of thermo-responsive structural units and further polymerizing these macroradicals in a second step with one or more than one ethylenically unsaturated monomer yielding hydrophilic structural units. The preparation of random and block copolymers of NIPAM and DMA with controlled molecular weight and molar composition is for instance described by K. Li and Y. Cao, Soft Materials, 8(3), 226-238, (2010).

The copolymers of the above-described kind are considered non-toxic and physiologically compatible. They have been found to be very efficient in the rapid and controlled dissolution and effective solubilization of poorly water soluble substances in aqueous media from solid mixtures.

By the term "poorly water soluble substance" it is referred in the context of the present invention to a substance having as such (i.e. without any additives) a solubility in deionized water of pH 7.0, of 200 mg/L or less, preferably 100 mg/L or less, more preferably 50 mg/L or less or 20 mg/L or less or 10 mg/L or less or 1 mg/L or less, at a temperature of 23° C. and an atmospheric pressure of 1 atm. Typically the poorly water soluble substance according to the present invention is an organic lipophilic substance with biological activity. Accordingly the poorly water soluble substance can in particular be selected from the group consisting of active pharmaceutical ingredients (APIs), active personal care agents, plant protective agents, insecticides and foodstuff.

The present invention is considered particularly useful for active pharmaceutical ingredients as poorly water soluble substances. The active pharmaceutical ingredient can generally be any substance for application in a therapeutic, diagnostic or prophylactic medical treatment of the human or animal body. The API may for instance be selected from the group of antihypertensives, anti-anxiety agents, anticlotting agents, anticonvulsants, blood glucose lowering agents, decongestants, antihistamines, antitussives, beta blockers, anti-inflammatories, antipsychotic agents, cognitive enhancers, cholesterol-reducing agents, antiobesity agents, autoimmune disorder agents, anti-impotence agents, antibacterial agents, antifungal agents, hypnotic agents, anti-Parkinsonism agents, anti-Alzheimer's disease agents, anti-depressants, antiviral agents, anti-atherosclerotic agents, glycogen phosphorylase inhibitors, hormones, vitamins, carotinoids, antiseptic agents, cytostatics, anesthetics, neuroleptics, antimycotics, spasmolytic agents, immunoglobines, sera, thyroid therapeutic agents, antihyperkinetic agents, ophthalmic agents, neuropathy agents, metabolic regulators, muscle relaxants, anti-lipemics, hepatic therapeutic agents, coronary agents, cardiacs, regulatory peptides and enzymes and their inhibitors, sedatives, gynecological agents, gout remedies, fibrinolytics, circulation-promoting agents, diuretics, diagnostic agents, corticoids, bile duct therapeutics, antiasthmatics, anti-epileptics, antidotes, antidiabetes agents, antiallergics, analgesics, analeptics, keratolytic agents, antipyretic agents and vasodilatory agents, without being limited thereto. The present invention is particularly useful when the API as such has too low solubility in aqueous media for effective use. This is commonly the case for class II drugs according to the Biopharmaceutics Classification System (BCS) as these substances typically suffer from an insufficient bioavailability.

Accordingly, a copolymer according to the present invention as described above or a combination of two or more thereof can be used as an ingredient in solid mixtures to increase the solubility and/or the dissolution rate of a poorly water soluble substance such as an API in an aqueous medium. The aqueous medium within the sense of the present invention can e.g. be water itself as well as any kind of aqueous solution, in particular any physiologically relevant aqueous solution. Physiologically relevant aqueous solutions are e.g. natural aqueous body fluids of humans, animals and plants, and artificially prepared aqueous solutions that mimic such body fluids or are representative of an aqueous medium in a certain physiological state, respectively. Examples of physiologically relevant aqueous solutions are for instance saliva, blood, gastric fluid, intestinal fluid, simulated gastric fluid, fasted state simulated intestinal fluid, fed state simulated intestinal fluid and other aqueous buffer and/or enzyme solutions simulating further physiological conditions.

According to the present invention, the term "solubility" generally encompasses the amount of substance, which is dissolved on a molecular level as well as the amount of substance, which is dispersed in the form of colloidal aggregates in the aqueous medium. "Colloidal aggregates" as used herein means entities, which are stably dispersed and do not settle from the solution even when exposed to substantial settling forces such as centrifugal forces of 16,100×g, where g is the acceleration due to gravity at the Earth's surface, for 1 min. The colloidal aggregates are typically of a size smaller than detectable with an optical microscope, e.g. having a length in their longest dimension in the range from 1 to 200 nm, preferably from 1 to 100 nm or from 1 to 50 nm. The solubility of a poorly water soluble substance in an aqueous medium can be determined quantitatively e.g. by high pressure liquid chromatography analysis as set forth in detail in the Examples.

The copolymers according to the invention may increase the solubility of poorly water soluble substances significantly in a comparable, for preferred kinds of the copolymers according to the present invention also in a substantially enhanced, manner with respect to state of the art solubilizers such as HPMCAS. A particular advantage is that they are capable of maintaining the resulting highly supersaturated state for substantial periods of time, e.g. for 6 hours or more, i.e. may effectively prevent re-precipitation. Accordingly the copolymers according to the present invention may concomitantly enhance the bioavailability of poorly water soluble substances such as lipophilic APIs e.g. by forming colloidal aggregates wherein the lipophilic substances may effectively be solubilized. The vehicles are stable in the surrounding aqueous medium and allow transporting the lipophilic substances in amounts significantly higher than without use of the copolymers to sites in a human or animal body or plant, where they exert their intended effect.

The compositions according to the present invention comprise a) at least one copolymer of the above described kind and b) at least one poorly water soluble substance as set forth above. The at least one copolymer a) and the at least one poorly water soluble substance b) are present herein as components of a solid mixture. Typically the compositions according to the present invention are themselves solid formulations. Nevertheless, the present invention also encompasses compositions, which are semisolid or liquid or aerosols and comprise the afore-mentioned solid mixture. In the context of the present invention the state of matter such as "solid", "semi-solid" or "liquid" refers to the state of matter at ambient conditions (23° C., 1 atm), if not indicated otherwise. Solid and semi-solid materials are generally able to maintain their shape and volume even when not confined. A solid material typically does not deform or flow under the effect of gravity. Semi-solid means that the material deforms and/or flows slowly when an external force such as gravity is applied. The solid and semi-solid state thus differ from the liquid state in that the latter is characterized by the material being flowable even in the absence of any external force and unable to retain the shape when not confined. Of course it is readily understood by the skilled artisan that a mass of discrete solid particles, such as a powder or a granular material, is classified as a solid material although only the individual particles retain their shape and volume when not confined, but not the entire mass.

The at least one copolymer a) and the at least one poorly water soluble substance b) can each be present in the solid mixture in various forms with respect to their dimensions, order, shape and distribution. For instance, suitable solid mixtures according to the present invention range from heterogeneous multiphase systems to homogeneous single phase systems. Heterogeneous multiphase system refers to a mixture, wherein the constituent components are present as discrete phases which retain their individual physical properties such as phase transition temperatures. Non-limiting examples of heterogeneous multiphase systems are e.g. blends of particulate materials, interpenetrating continuous solid phases or solid dispersions of one or more particulate material in a continuous solid matrix. If the solid mixture comprises blended or dispersed substance(s) b) and/or copolymers a) these can each independently be of any possible shape such as spherical, cuboid, needle-like or irregular shape, and dimensions such as having an average particle size in the range of 1 nm to 5 mm, e.g. 1 nm to 200 nm, or 10 nm to 500 nm, or 100 nm to 1 µm, or 1 µm to 300 µm, or 20 µm to 500 µm, or 50 µm to 1 mm, or 0.2 to 1 mm. Herein, average particle size refers to the diameter of the smallest circle completely encompassing a particle determined from two-dimensional images acquired by electron or optical microscopy as a number average value over at least 50 particles. Homogeneous single phase system means on the other hand a mixture, wherein the constituent components are evenly distributed throughout the material on a molecular level and the mixture behaves as a uniform single phase exhibiting its own characteristic macroscopic properties e.g. a single glass transition temperature, which can be different from the glass transition temperatures of the distinct components used to prepare the mixture. In other words, the at least one copolymer a) and the at least one poorly water soluble substance b) can form a true solid solution. According to the present invention the solid mixture is typically a solid dispersion or a solid solution of the at least one poorly water soluble substance b) in the at least one copolymer a).

The at least one poorly water soluble substance can be present in the compositions according to the present invention at least partly in amorphous form. Usually the amorphous form of poorly water soluble substances dissolves inherently better in aqueous media than crystalline forms. The copolymers of the above-described kind have been found to efficiently inhibit the crystallization of poorly water soluble substances. Herein, crystallization can be inhibited in the solid state, i.e. the copolymer may stabilize the amorphous form of a poorly water soluble substance in solid mixture against the thermodynamically favored transition to the crystalline form, and/or crystallization can be inhibited in aqueous solution, i.e. the copolymer may stabilize the solubilized poorly water soluble substance against nucleation and re-precipitation. Preferably the at least one poorly water soluble substance is predominantly, e.g. more than 50 wt. % or more than 80 wt. % or more than 90 wt. % or more than 95 wt. % of the total mass of the respective poorly water soluble substance, or completely present in amorphous form in the composition according to the present invention.

In addition to the at least one copolymer a) of the above-described kind and the at least one poorly water soluble substance b) the composition according to the present invention may optionally comprise one or more than one additive. Any conventional additive used in compositions for the respective intended application, e.g. pharmaceutical composition, known from the prior art can be employed as long as they do not interfere with the desired action of the poorly water soluble substance(s) and do not adversely affect the above-described favorable effects imparted by the copolymers (a). The composition according to the present invention may comprise e.g. one or more than one additive selected from the group consisting of fillers, binders, pH regulators, solvents, surfactants, antioxidants, preservative agents, plasticizers, colouring agents, flavouring agents, mineral adjuvants, emollients, lubricants, perfumes, excipients other than the copolymers a) of the above-described kind and combinations of any of the foregoing. Suitable antioxidants can be exemplified by ascorbic acid, citric acid, vitamin E and derivatives of these compounds, as well as butylated hydroxyanisole. As plasticizer for instance mineral oils, petrolatum, lanolin, polyethylene glycol, polypropylene glycol, sorbitol, triethanol amine, benzyl benzoate, dibutyl sebacate, diethyl phthalate, glyceryl monostearate, triacetin and/or triethyl citrate could be used. Suitable solvents are e.g. water, alcohols such as ethanol, isopropyl alcohol, ethylene glycol, propylene glycol, polyethylene glycol, polypropylene glycol and glycerol. Eligible pH regulators can preferably be all types of physiologically acceptable acids and/or bases. Suitable surfactants can be nonionic, cationic, anionic or of the betain type. For example fatty alcohol sulfates, fatty alcohol sulfonates, fatty alcohol ether sulfates, fatty alcohol ether sulfonates, fatty alcohol alkoxylates, fatty alcohol phosphates, fatty acid sulfonates, alkyl sulfonates, alkyl polyglycosides, sorbitan esters and alkoxylated derivatives thereof, sugar fatty acid esters, fatty acid polyglycerol esters, fatty acid partial glycerides, fatty acid carboxylates, fatty alcohol succinates, quarternary ammonium compounds, alkylphenol alkoxylates or mixtures thereof could be used, without being limited thereto. Fillers that may be incorporated in the pharmaceutical composition of the present invention e.g. to modify the consistency or appearance include, without being limited thereto, for instance pigments, titania, alumina, silica, zinc oxide, magnesium stearate, silicates, alumosilicates, clay, talc, waxes and polymers such as cellulose derivatives like methyl cellulose, ethyl cellulose, hydroxyethyl cellulose or hydroxypropyl methyl-cellulose. Excipients other than the copolymers according to the present invention can be exemplified for instance by the substances mentioned as excipients in the Handbook of Pharmaceutical Excipients, Third Edition, Edited by A. H. Kibbe, American Pharmaceutical Association and Pharmaceutical Press (2000), WO 00/76482 and Tables 3-5 in E. T. Cole et al., Advanced Drug Delivery Reviews 60 (2008), 747-756.

The composition according to the present invention typically comprises the at least one copolymer a) and the at least one poorly water soluble substance b) together in an amount corresponding to 1 to 100 wt. %, preferably at least 10 wt. %, more preferably at least 50 wt. % or at least 80 wt. %, based on the total weight of the composition. The balance may then be made of the afore-mentioned optional additives, if any. The additives may thus e.g. be comprised in the composition according to the present invention in a total amount corresponding to 0 to 99 wt. %, preferably 0 to 90 wt. % or 0 to 50 wt. % or 0 to 20 wt. %, based on the total weight of the composition. The at least one copolymer a) and the at least one poorly water soluble substance b) are typically comprised in the compositions according to the present invention in a weight ratio in the range from 100:1 to 1:10, preferably from 20:1 to 1:2, more preferably in the range from 10:1 to 1:1. Typically the at least one copolymer a) is present in the composition according to the present invention in an amount of ≥10 wt. %, preferably ≥20 wt. %, more preferably ≥30 wt. % or ≥50 wt. %, such as in a range from 10 to 99 wt. % or from 40 to 70 wt. %, based on the total weight of the composition. The at least one poorly water soluble substance b) is typically comprised in the compositions according to the present invention in an amount of at least 1 wt. % such as an amount in the range from 1 to 60 wt. %, preferably 5 to 40 wt. %, more preferably 10 to 30 wt. %, based on the total weight of the composition. In a specific non-limiting example the composition of the present invention comprises 60 to 95 wt. % of the one or more than one copolymer a) and 5 to 40 wt. % of one or more than one poorly water soluble substance b), based on the total weight of the composition.

The above-mentioned favorable dissolution and solubilization characteristics of the compositions according to the present invention are retained over considerable periods of time under typical storage conditions evidencing the physical and chemical stability of the inventive formulations comprising at least one copolymer a) of the above-described kind in solid mixture with at least one poorly water soluble substance.

The compositions according to the present invention can be prepared using conventional techniques and equipment known as such from the prior art. Solid mixtures of one or more than one copolymer a) of the above-described kind with at least one poorly water soluble substance b) can for instance be obtained by blending powders of the constituent materials. Solid mixtures in the form of fine solid dispersions or solid solutions are e.g. obtainable by solution-based methods such as co-precipitation and spray drying. For spray drying a solution or dispersion comprising the at least one copolymer a) and the poorly water soluble substance b) may be provided and sprayed into a heated gaseous drying medium to evaporate the solvent. Alternatively, also freeze-drying can be applied. Details of the spray drying process can e.g. be found in R. H. Perry, D. W. Green, J. O. Maloney eds., Perry's Chemical Engineers' Handbook, $6^{th}$ edition, McGraw-Hill Book Co. 1984, pages 20-57. Co-precipitation can be carried out for instance by dissolving the at least one copolymer a) and the at least one poorly water soluble substance b) in a mutual solvent and subsequent mixing with a non-solvent or by removing the solvent again through evaporation. Another possibility is to provide a first solution of the copolymer component in a first solvent and a second solution of the poorly water soluble substance(s) in a second solvent. The first solvent and the second solvent are selected in such a manner that the solubility of both components is sufficiently low in the mixture of the first and the second solvent. Thus the copolymer(s) a) and the poorly water soluble substance(s) b) can be co-precipitated by mixing both solutions. Furthermore the at least one copolymer a) and the one or more than one poorly water soluble substance b) may be formed into solid mixtures by a melt process. For instance the one or more than one poorly water soluble substance may be dispersed or dissolved in a melt of the one or more than one copolymer a) using conventional polymer melt processing techniques. The resulting solid mixture of the one or more than one copolymer a) and the at least one poorly water soluble substance b) can optionally be combined with further ingredients to form the composition according to the present invention. For instance the solid mixture can be combined with or incorporated in a suitable carrier medium such as a solid or gel matrix, a liquid or a carrier gas and/or additives of any of the above-mentioned type can be combined with said solid mixture. The optional additives, if any, may also be incorporated into the solid mixture at any suitable stage during the preparation of the solid mixture such as by including them into the precursor solution(s) or dispersion(s) or the feedstock(s) for melting or by adding them during the stage wherein the mixture of the copolymer component and the poorly water soluble substance(s) is formed.

The compositions according to the present invention as prepared by any one of these preparation processes are typically obtained in solid form e.g. as a powder or solidified extrudate and may thus be in particular conveniently used to provide solid dosage forms comprising a composition according to the present invention. In particular in pharmaceutical applications it is important to provide the active pharmaceutical ingredients (APIs) in a dosage form, which enables convenient handling and administration. The solid dosage form can e.g. be a powder, a lozenge, a suppository, a tablet or a filled capsule.

For oral administration tablets and capsules enjoy commonly good acceptance among most patients and are thus preferably used as API delivery system. Tablets comprising the composition of the present invention may e.g. readily be prepared by conventional pressing of the raw powder or melt extrusion of the composition and re-solidification using dies of the desired tablet size and shape. Capsules filled with the composition according to the present invention may be prepared using processing techniques and equipment, which is per se known from the prior art, e.g. from E. T. Cole, Advanced Drug Delivery Reviews 60 (2008), 747-756.

Owing to the rapid dissolution and efficient solubilization of APIs, which are as such only poorly waters soluble, from solid mixtures with the copolymers according to the present invention an effective dose as required for most medical applications in-vivo can be provided by a single unit of a tablet or capsule of conventional size and within a short time from administration.

The present invention will be illustrated in more detail by the following Examples, however, the invention is not meant to be limited to these Examples.

EXAMPLES

Example 1

Preparation of copolymers of N-isopropylacrylamide (NIPAM) and N,N-dimethylacrylamide (DMA)

Random copolymers of N-isopropylacrylamide (NIPAM) and N,N-dimethylacrylamide (DMA) of different number average molecular weight and different composition with respect to the molar proportion of structural units derived from NIPAM and from DMA, respectively, were prepared by controlled radical polymerization using either 4-cyano-4-(propylsulfanylthiocarbonyl) sulfanylpentanoic acid (CPP) or 4-cyano-4-[(dodecylsulfanylthiocarbonyl)sulfanyl]pentanoic acid (CDP) as a chain transfer agent (CTA), or by free radical polymerization without either CTA.

CPP was synthesized according to the procedure described in Macromolecules 2008, 41, 8429-8435 except that $Na_2SO_4$ instead of $MgSO_4$ was used for drying after extraction. NIPAM (≥99%), DMA (99%), CDP (97%), and the initiator azobisisobutyronitrile (AIBN, 98%) were obtained from Aldrich and used without further purification. Anisole (≥99%) was obtained from Fluka and used without further purification. Dimethylsulfoxide (DMSO, 99.9%) was used as received from Fisher. 1,4-Dioxane (99+%, extra pure stabilized with 5-30 ppm butylated hydroxytoluene) was used as received from Acros Organics.

For examples 1-1 through 1-16, copolymers of NIPAM and DMA with different composition were prepared in a semi-continuous parallel pressure reactor (ScPPR from Freeslate) with Library Studio software to designate the operating parameters and Automation Studio software to operate the reactor. For each synthesis the respective amounts of NIPAM, AIBN, CDP, anisole, and DMSO as listed in Table 1 were introduced into a 10 mL reaction tube as solutions in dioxane. NIPAM and anisole, which was used as an internal standard for monomer conversion calculations for crude reaction mixtures prior to precipitation, were introduced together in dioxane with NIPAM comprising 40% by weight and anisole comprising 4% by weight of the total feed solution. DMA and DMSO (internal standard) were similarly introduced together in dioxane, with DMA comprising 40% by weight and DMSO comprising 4% by weight of the total feed solution. AIBN was introduced as a 0.398% by weight solution in dioxane. CDP was introduced as a 2% by weight solution in dioxane. Additional dioxane was added to each vial to attain the total amount listed in Table 1. Nitrogen was bubbled through the reaction mixture for 45 min. Thereafter the reaction vials were heated in the thermostated steel reactor holders to 70° C. and held at this temperature for 7 h. Subsequently, the reaction mixture was cooled to 0° C. and the vials opened to air. Each formed polymer was isolated from the reaction mixture by precipitation in 300 mL THF. The thus obtained precipitate solid product was re-dissolved in 5 mL methanol, precipitated in THF as set forth above a second time, and filtered under vacuum. The solid product was washed with 10-15 mL diethyl ether and subsequently dried for at least 12 h under vacuum at about 10 mTorr to yield the respective purified NIPAM-co-DMA polymer.

For Examples 1-17 through 1-20, NIPAM, DMA and CPP were charged in the respective amounts indicated in Table 1 into a single neck pear shaped flask. 14.5 mL of 1,4-dioxane were added into the flask and the reaction mixture was sonicated until a homogenous solution was formed. Subsequently the respective amount of AIBN listed in Table 1 was added to the reaction mixture by adding the corresponding amount of a stock solution made by dissolving 50 mg of AIBN in 1 mL of 1,4-dioxane. After bubbling nitrogen through the solution for 45 minutes, the reaction mixture was heated to a temperature of 70° C. by means of a thermostated oil bath and stirred at this temperature for 6 hours. Thereafter the resulting copolymer was precipitated from the reaction mixture by precipitation in about 300 mL diethyl ether. The obtained precipitate was purified by dissolving it in tetrahydrofuran (THF) and re-precipitation in about 300 mL diethyl ether yielding the of purified NIPAM-co-DMA polymer.

For Example 1-24, in which a free radical polymerization was conducted to compare to the Examples produced via controlled radical polymerization, a procedure analogous to that used for Examples 1-17 through 1-20 was followed with the following modifications: 7.2 mL of dioxane was used and the reaction was stirred at 70° C. for 7 h.

Homopolymers of NIPAM and DMA were prepared analogously to Examples 1-17 through 1-20 for comparative reasons using either only NIPAM or only DMA as monomer instead of a mixture of NIPAM and DMA (cf. Examples 1-22 and 1-23 of Table 1).

A block copolymer of NIPAM and DMA was synthesized as follows for Example 1-21, first by preparing macroinitiator homopolymer PNIPAM-CPP followed by polymerization of DMA. A 50 ml round conical flask was charged with NIPAM (5 g, 44.9 mmol), CPP (357 mg, 0.88 mmol), AIBN (7.2 mg, 0.044 mmol), and 1,4-dioxane (22 mL). The reaction mixture was degassed for 45 min by bubbling nitrogen. The reaction flask was subjected to preheated oil bath at 70° C. for 6 h. PNIPAM-CPP was isolated by precipitation into pentane (400 mL), redissolution of the polymer in THF, and a second precipitation in pentane (400 mL), then by dialysis against water. The final solid product was isolated by removal of the water through freeze drying. The calculated $M_n$ of PNIPAM-CPP was 6 kDa by SEC (THF). To synthesize block copolymer, a flask was charged with PNIPAM-CPP (1 g, 0.167 mmol), AIBN (5.5 mg, 0.033 mmol), DMA (3.31 g, 33 mmol), and 1,4-dioxane (16.7 mL). The reaction mixture was degassed for 45 min by bubbling nitrogen. The reaction flask was subjected to preheated oil bath at 70° C. for 5 h. The reaction mixture was dialyzed against water in 1000 Da cut off membrane tubing. The final solid product was isolated by removal of the water through freeze drying. The calculated $M_n$ of PNIPAM-b-PDMA was 25.6 kDa by SEC (THF).

Example 2

Preparation of Random Copolymers of N-isopropylacrylamide (NIPAM) and 4-vinyl-pyrrolidone (VP)

A series of copolymers of N-isopropylacrylamide (NIPAM) and 4-vinyl-pyrrolidone (VP) was obtained as follows: For each synthesis NIPAM (Aldrich, >99%) and VP (Aldrich, ≥99.9%, purified by distillation under vacuum and stored at −20° C. under nitrogen) were introduced to a round bottom flask in the respective amounts indicated in Table 2 together with 10 mg of AIBN (Aldrich, 98%) and 15 mL of dimethylformamide (DMF, Aldrich, ≥99.8%). The reaction mixture was flushed with nitrogen gas for at least 30 minutes. Subsequently the stirred reaction mixture was heated by a thermostated oil bath to 70° C. and maintained at this temperature for 5 h. Thereafter the reaction mixture was cooled to 0° C. and the flask opened to air. The resulting copolymer was isolated from the reaction mixture by precipitation with about 500 mL diethyl ether followed by filtration under vacuum on a Büchner funnel. The obtained solid product was re-dissolved in methanol, precipitated and filtered under vacuum as set forth above a second time. The thus obtained solid product was washed with about 300 mL diethyl ether three times to remove residual monomer and DMF and dried under vacuum at 40° C. for at least 24 h to yield the respective NIPAM-co-VP polymer.

TABLE 1

Amounts of substances used in the preparation of NIPAM-co-DMA polymers, molar fractions of structural units derived from NIPAM and DMA, respectively, in the resulting polymer as determined by NMR spectrometry, and number average molecular weight ($M_n$) and polydispersity index (PDI) of the resulting polymer as determined by SEC and the LCST in deionized water and a phosphate buffer saline with FaSSIF determined as described below.

| Example | m(NIPAM) [g] | m (DMA) [g] | m (CTA) [mg] | m (AIBN) [mg] | m (Anisole) [mg] | m (DMSO) [mg] | m (Dioxane) [g] | mol % NIPAM | mol % DMA | Mn [g/mol] | PDI | LCST in water (° C.) | LCST in PBS + SIF (° C.) |
|---|---|---|---|---|---|---|---|---|---|---|---|---|---|
| 1-1 | 1.11 | 0.42 | 56.0 | 5.0 | 110.8 | 41.6 | 6.27 | 66 | 34 | 10.950 | 1.04 | 48.3 | 45.8 |
| 1-2 | 1.11 | 0.42 | 28.0 | 2.5 | 110.8 | 41.6 | 6.29 | 66 | 34 | 20.000 | 1.06 | n/a | 39.4 |
| 1-3 | 1.11 | 0.42 | 18.7 | 1.7 | 110.8 | 41.6 | 6.29 | 67 | 33 | 30.000 | 1.09 | n/a | 38.7 |
| 1-4 | 1.11 | 0.42 | 14.0 | 1.2 | 110.8 | 41.6 | 6.30 | 65 | 35 | 42.000 | 1.14 | n/a | 38.0 |
| 1-5 | 1.11 | 0.42 | 11.0 | 1.0 | 110.8 | 41.6 | 6.31 | 66 | 34 | 69.000 | 1.17 | n/a | 37.2 |
| 1-6 | 1.11 | 0.42 | 9.0 | 0.8 | 110.8 | 41.6 | 6.31 | 68 | 32 | 54.500 | 1.21 | n/a | 36.5 |
| 1-7 | 0.16 | 1.25 | 28.0 | 2.5 | 16.0 | 124.8 | 6.43 | 8 | 92 | 20.600 | 1.05 | n/a | n/a |
| 1-8 | 0.32 | 1.11 | 28.0 | 2.5 | 31.6 | 111.2 | 6.41 | 19 | 81 | 17.900 | 1.05 | n/a | n/a |
| 1-9 | 0.48 | 0.83 | 28.0 | 2.5 | 47.6 | 83.2 | 6.53 | 30 | 70 | n/a | n/a | n/a | 79.8 |
| 1-10 | 0.63 | 0.69 | 28.0 | 2.5 | 63.2 | 69.2 | 6.51 | 42 | 58 | 19.600 | 1.20 | n/a | 62.3 |
| 1-11 | 0.79 | 0.56 | 28.0 | 2.5 | 79.2 | 55.6 | 6.50 | 54 | 46 | 14.300 | 1.13 | n/a | 50.2 |
| 1-12 | 0.95 | 0.42 | 28.0 | 2.5 | 95.2 | 41.6 | 6.47 | 63 | 37 | 17.800 | 1.06 | n/a | 42.3 |
| 1-13 | 1.03 | 0.49 | 28.0 | 2.5 | 102.8 | 48.4 | 6.31 | 63 | 37 | 18.900 | 1.06 | n/a | 42.7 |
| 1-14 | 1.19 | 0.35 | 28.0 | 2.5 | 118.8 | 34.8 | 6.29 | 73 | 27 | 17.700 | 1.07 | n/a | 37.2 |
| 1-15 | 1.27 | 0.28 | 28.0 | 2.5 | 126.8 | 27.6 | 6.27 | 76 | 24 | 11.300 | 1.08 | n/a | 35.4 |
| 1-16 | 1.43 | 0.14 | 28.0 | 2.5 | 142.4 | 14.0 | 6.25 | 90 | 10 | n/a | n/a | n/a | 32.0 |
| 1-17 | 0.82 | 2.14 | 40.0 | 4.8 | — | — | 15.0 | 23 | 77 | 26.000 | 1.28 | >90 | >90 |
| 1-18 | 1.63 | 1.43 | 40.0 | 4.8 | — | — | 15.0 | 45 | 55 | 24.000 | 1.10 | 71 | 53.5 |
| 1-19 | 2.45 | 0.71 | 40.0 | 4.8 | — | — | 15.0 | 70 | 30 | 25.000 | 1.04 | 55 | 37 |
| 1-20 | 2.77 | 0.42 | 40.0 | 4.8 | — | — | 15.0 | 86 | 14 | 25.000 | 1.20 | 30 | n/a |
| 1-21 | 1 g of PNIPAAm-CTA (6 kDa) | 3.31 | 1 g of PNIPAAm-CTA (6 kDa) | 5.5 | — | — | 17.2 | 27 | 73 | 25.600 | 1.18 | n/a | n/a |
| 1-22 (Comp.) | 5 | 0 | 44.0 | 3.6 | — | — | 15.0 | 100 | 0 | 22.000 | 1.23 | 28 | n/a |
| 1-23 (Comp.) | 0 | 5 | 70.0 | 8.3 | — | — | 15.0 | 0 | 100 | 20.200 | 1.18 | None | None |
| 1-24 | 1.11 | 0.43 | 0 | 15.0 | — | — | 7.5 | 76 | 24 | 150,000 | 1.82 | n/a | 34.3 | n/a: not available

TABLE 2

Amounts of monomers used in the preparation of NIPAM-co-VP polymers, yield of polymer, molar fractions of structural units derived from NIPAM and VP, respectively, in the resulting polymer as determined by NMR spectrometry, the number average molecular weight ($M_n$) and polydispersity index (PDI) of the resulting polymer as determined by SEC and the LCST in a phosphate buffer saline with FaSSIF determined as described below.

| Example | m(NIPAM) [g] | V(VP) [mL] | Yield [g] | mol % NIPAM | mol % VP | Mn [g/mol] | PDI | LCST in PBS [° C.] |
|---|---|---|---|---|---|---|---|---|
| 2-1 | 2.55 | 0.80 | 2.38 | 74 | 26 | 108,000 | 1.44 | 37 |
| 2-2 | 2.04 | 1.28 | 2.92 | 61 | 39 | 158,000 | 1.34 | 42 |
| 2-3 | 1.70 | 1.60 | 1.95 | 49 | 51 | 326,000 | 1.37 | 44 |

TABLE 2-continued

Amounts of monomers used in the preparation of NIPAM-co-VP polymers, yield
of polymer, molar fractions of structural units derived from NIPAM and
VP, respectively, in the resulting polymer as determined by NMR spectrometry,
the number average molecular weight ($M_n$) and polydispersity index (PDI)
of the resulting polymer as determined by SEC and the LCST in a phosphate
buffer saline with FaSSIF determined as described below.

| Example | m(NIPAM) [g] | V(VP) [mL] | Yield [g] | mol % NIPAM | mol % VP | Mn [g/mol] | PDI | LCST in PBS [° C.] |
|---|---|---|---|---|---|---|---|---|
| 2-4 | 1.36 | 1.92 | 2.85 | 42 | 58 | 220,000 | 1.22 | 47 |
| 2-5 | 0.85 | 2.40 | 2.97 | 26 | 74 | 370,000 | 2.44 | 52 | n/a: not available

Example 3

Preparation of Random Copolymers of NIPAM and Acrylamide (AA)

Several copolymers of N-isopropylacrylamide (NIPAM, Aldrich, ≥99%) and acrylamide (AA, Aldrich, ≥98%) with different composition were prepared in a semi-continuous parallel pressure reactor (ScPPR from Freeslate) analogously to Examples 1-1 through 1-16. For each synthesis the respective amounts of NIPAM, AIBN (Sigma, 98%), CDP, anisole, and DMSO as listed in Table 3 were introduced into a 10 mL reaction tube as solutions in a solvent mixture of 7:3 v:v dimethylformamide (DMF, Fisher Scientific, 99.9%):deionized water. NIPAM and anisole, which was used as an internal standard for monomer conversion calculations for crude reaction mixtures prior to precipitation, were introduced together in a 7:3 (v:v) mixture of DMF:water, with NIPAM comprising 40% by weight of the total feed solution and anisole comprising 2% by weight of the total feed solution. AA and DMSO were similarly introduced together in a second mixture of 7:3 (v:v) DMF:water, with AA comprising 40% by weight of the total feed solution and DMSO comprising 2% by weight of the total feed solution. AIBN was introduced as a 0.398% by weight solution in 7:3 (v:v) DMF:water. CDP was introduced as a 2% by weight solution in DMF. Additional water and DMF:water (7:3 v:v) mixture were added to bring the total mass of each component to the values presented in Table 3. Each formed polymer was isolated from the reaction mixture by precipitation in 300 mL THF. The thus obtained precipitate solid product was re-dissolved in 5 mL methanol, precipitated in THF as set forth above a second time and filtered under vacuum. The solid product was washed with 10-15 ml of mL diethyl ether and subsequently dried for at least 12 hours under vacuum at about 10 mTorr to yield the respective purified NIPAM-co-AA polymer.

Example 4

Preparation of Random Copolymers of NIPAM and 2-hydroxyethyl-methacrylate (HEMA)

Copolymers of N-isopropylacrylamide (NIPAM, Aldrich, ≥99%) and 2-hydroxyethyl-methacrylate (HEMA, Aldrich, ≥99%) with different composition were prepared according to the procedure described above in the context of Example 3 with the difference that HEMA was used instead of acrylamide, dioxane (Aldrich, 99.8%) was used as solvent instead of a DMF-water mixture and that precipitation was carried out using diethyl ether (Aldrich, ≥99.0%) instead of THF. The amounts of the substances used in the preparation of the different copolymers of N-isopropylacrylamide and 2-hydroxyethyl-methacrylate are summarized in Table 4.

TABLE 3

Amounts of substances used in the preparation of NIPAM-co-AA polymers, yield of polymer, molar fractions of structural
units derived from NIPAM and AA, respectively, in the resulting polymer as determined by NMR spectrometry, the number average
molecular weight ($M_n$) and polydispersity index (PDI) of the resulting polymer as determined by SEC and the LCST
in deionized water and a phosphate buffer saline with FaSSIF determined as described below.

| Example | m(NIPAM) [g] | m (AA) [g] | m (AIBN) [mg] | m (CDP) [mg] | m (DMSO) [mg] | m (Anisole) [mg] | m (DMF:H₂O, 7:3 v:v) [g] | Yield [g] | mol % NIPAM | mol % AA | Mn [g/mol] | PDI | LCST in H₂O [° C.] | LCST in PBS [° C.] |
|---|---|---|---|---|---|---|---|---|---|---|---|---|---|---|
| 3-1 | 0.48 | 0.70 | 2.5 | 28.0 | 34.8 | 23.8 | 6.50 | 0.998 | 27 | 73 | 17,500 | 1.04 | >100 | >100 |
| 3-2 | 0.63 | 0.60 | 2.5 | 28.0 | 29.8 | 31.6 | 6.50 | 1.013 | 36 | 64 | 23,800 | 1.03 | >100 | >100 |
| 3-3 | 0.79 | 0.50 | 2.5 | 28.0 | 24.8 | 39.6 | 6.50 | 1.060 | 45 | 55 | 18,500 | 1.04 | >100 | >100 |
| 3-4 | 0.95 | 0.40 | 2.5 | 28.0 | 20.0 | 47.6 | 6.50 | 0.876 | 57 | 43 | 23,400 | 1.05 | >100 | 74 |
| 3-5 | 1.11 | 0.30 | 2.5 | 28.0 | 15.0 | 55.4 | 6.50 | 0.930 | 65 | 35 | 19,900 | 1.05 | 75 | 56 |
| 3-6 | 1.27 | 0.20 | 2.5 | 28.0 | 10.0 | 63.4 | 6.50 | 0.370 | 73 | 27 | 21,700 | 1.03 | 50 | 45 | n/a: not available

TABLE 4

Amounts of substances used in the preparation of NIPAM-co-HEMA polymers, yield of polymer, molar fractions of structural units derived from NIPAM and HEMA, respectively, in the resulting polymer as determined by NMR spectrometry, and number average molecular weight ($M_n$) and polydispersity index (PDI) of the resulting polymer as determined by SEC.

| Example | m(NIPAM) [g] | m (HEMA) [g] | m (AIBN) [mg] | m (CDP) [mg] | m (DMSO) [mg] | m (Anisole) [mg] | m (dioxane) [g] | Yield [g] | mol % NIPAM | mol % HEMA | Mn [g/mol] | PDI |
|---|---|---|---|---|---|---|---|---|---|---|---|---|
| 4-1 | 1.11 | 0.55 | 2.5 | 28.0 | 27.4 | 55.4 | 6.00 | 1.010 | 67 | 33 | 25,200 | 1.01 |
| 4-2 | 1.27 | 0.36 | 2.5 | 28.0 | 18.2 | 63.4 | 6.00 | 1.110 | 78 | 22 | 26,300 | 1.04 |

Example 5

Preparation of Random Copolymers of N,N-diethylacrylamide (DEA) and N,N-dimethylacrylamide (DMA)

Copolymers of N,N-diethylacrylamide (DEA, Aldrich, 99%) and N,N-dimethylacrylamide (DMA, Aldrich, 99%) with different composition were prepared according to the procedure described above in the context of Example 3 with the difference that DEA was used instead of NIPAM, DMA was used instead of acrylamide, dioxane (Aldrich, 99.8%) was used as solvent instead of a DMF-water mixture and that precipitation was carried out using hexane (Aldrich, 95%) instead of THF. The amounts of the substances used in the preparation of the different copolymers of N,N-diethylacrylamide and N,N-dimethylacrylamide are summarized in Table 5.

deuterated chloroform as solvent on a Bruker AVANCE 400 MHz spectrometer equipped with a 10 mm cryoprobe without sample spinning at 25° C. using at least 672 scans, 40 s relaxation delay, 12.1 ms 90° pulse length, spectrum center: 100 ppm, spectral width: 250 ppm (for Examples 5-1 and 5-2) or on a Bruker AVANCE III HD 600 MHz spectrometer with a standard 10 mm probe without sample spinning at 25° C. using at least 1600 scans, a 40 s relaxation delay, 12.1 ms 90° pulse length, spectrum center: 100 ppm, spectral width: 250 ppm (for Examples 5-3, 5-4 and 5-5). The peaks were referenced to chloroform at 77.2 ppm.

The molar contents of structural units derived from the different monomers used to prepare the respective copolymer (homopolymers: 100 mol % of structural units derived from monomer used to prepare the homopolymer) were calculated from the ratio of integrated peak areas attributed to certain structural elements:

TABLE 5

Amounts of substances used in the preparation of DEA-co-DMA polymers, yield of polymer, molar fractions of structural units derived from DEA and DMA, respectively, in the resulting polymer as determined by NMR spectrometry, the number average molecular weight ($M_n$) and polydispersity index (PDI) of the resulting polymer as determined by SEC and the LCST in deionized water and a phosphate buffer saline with FaSSIF determined as described below.

| Example | m(DEA) [g] | m (DMA) [g] | m (AIBN) [mg] | m (CDP) [mg] | m (DMSO) [mg] | m (Anisole) [mg] | m (dioxane) [g] | Yield [g] | mol % DEA | mol % DMA | Mn [g/mol] | PDI | LCST in H₂O [° C.] | LCST in PBS [° C.] |
|---|---|---|---|---|---|---|---|---|---|---|---|---|---|---|
| 5-1 | 0.36 | 1.11 | 2.5 | 28.0 | 55.6 | 17.8 | 6.00 | 0.81 | 20 | 80 | 22,700 | 1.06 | n/a | n/a |
| 5-2 | 0.71 | 0.83 | 2.5 | 28.0 | 41.6 | 35.6 | 6.00 | 0.96 | 40 | 60 | 21,700 | 1.04 | 77 | 67 |
| 5-3 | 0.89 | 0.69 | 2.5 | 28.0 | 34.6 | 44.6 | 6.00 | 1.22 | 50 | 50 | 23,600 | 1.06 | 61 | 57 |
| 5-4 | 1.16 | 0.48 | 2.5 | 28.0 | 24.2 | 57.8 | 6.00 | 1.23 | 65 | 35 | 15,400 | 1.04 | 50 | 45 |
| 5-5 | 1.42 | 0.28 | 2.5 | 28.0 | 13.8 | 71.2 | 6.00 | n/a | 81 | 19 | 28,600 | 1.07 | 41 | 37 |

N/a: not available

Characterization of the Prepared Polymers

The prepared polymers were investigated by nuclear magnetic resonance (NMR) spectrometry and size exclusion chromatography (SEC) as well as with respect to their thermo-responsive properties according to the procedures set forth below in order to obtain information about their chemical composition, molecular weight distribution, and LCST, respectively.

A) Characterization by NMR Spectrometry

Figure 2:
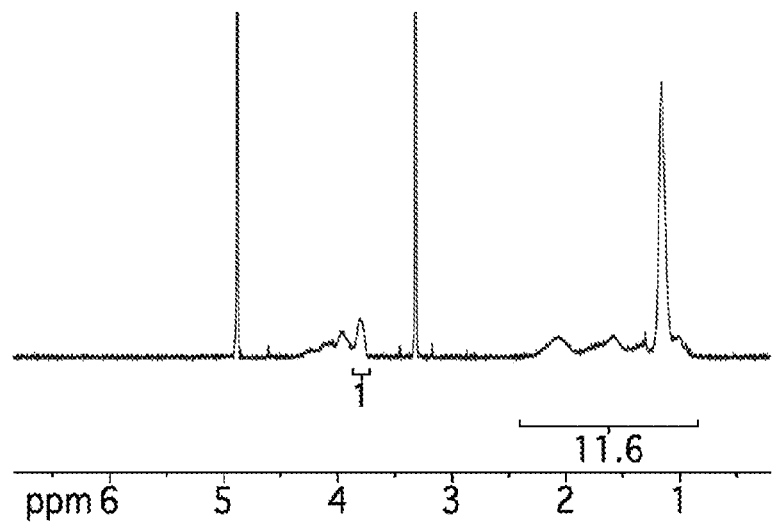
FIG. 2 shows the $^1$H-NMR spectrum (500 MHz, CD$_3$OD) of a NIPAM-co-HEMA polymer (polymer of Example 4-1) having a backbone constituted of about 67 mol % structural units derived from NIPAM and about 33 mol % structural units derived from HEMA as calculated from the ratio of the indicated relative integrated peak areas according to the procedure outlined in the Examples.

¹H-NMR spectra were acquired on a Bruker Avance III HD 500 spectrometer equipped with a 5 mm Prodigy TCI cryoprobe with z-axis gradients at 22° C. using a 10 second relaxation delay and at least 16 transients without spinning to reduce signal-to-noise ratio in CDCl₃ (for Examples 1-1 to 1-24 and Examples 2-1 to 2-5), deuterated methanol (for Examples 3-1 to 3-6 and Examples 4-1 to 4-2) or D₂O (for Examples 5-1 to 5-5), respectively. For poly(DEA-co-DMA) additionally ¹³C-NMR spectra were acquired in a) Poly(NIPAM-co-DMA): The molar fraction of structural units derived from NIPAM or DMA, respectively, in the copolymer backbone was calculated from the integrated area of the peak at about 4.1 ppm related to the proton of the N—CH moiety of the NIPAM units (1 H) in proportion to the integrated area of the peaks in the range of about 2.8-3.3 ppm related to the protons of the N—(CH₃)₂ moiety of the DMA units (6H) in the ¹H-NMR spectra. For the sake of illustration, FIG. 1 shows the ¹H-NMR spectrum of the copolymer of Example 1-6 in CDCl₃. The indicated integrated peak areas are reported relative to the integrated area of the peak at about 4.1 ppm (integrated peak area: 1.00). The integrated peak area of the peaks in the range of about 2.8-3.3 ppm attributed to the protons of the N—(CH₃)₂ moiety of the DMA units is about 2.86. As there are six protons of the N—CH₃ type per DMA structural unit an integrated area value of 0.48 per such proton can be calculated. Thus from the relative integrated peak area per proton for both types of considered structural units, the molar fraction of NIPAM-derived structural units in the copolymer can be deduced as 1.00/(1.00+0.48)=68 mol % and the molar fraction of DMA-derived structural units in the copolymer follows as 0.48/(1.00+0.48)=32 mol %.

b) Poly(NIPAM-co-VP): The molar fraction of the structural units derived from NIPAM or VP, respectively, in the polymer backbone was calculated from the integrated area of the peak at about 1.1 ppm (protons of the C—(CH$_3$)$_2$ moiety of the NIPAM units, 6H) in proportion to the integrated area of the peak at about 3.2 ppm (protons of the C=CH$_2$ moiety of VP, 2H) in the $^1$H-NMR spectra analogously to the procedure discussed above for poly(NIPAM-co-DMA).

c) Poly(NIPAM-co-HEMA): The molar fraction of the structural units derived from NIPAM or HEMA, respectively, in the polymer backbone was calculated from the integrated area of the peak at about 3.8 ppm (carbon-bound protons of the CH$_2$OH moiety of the HEMA units, 2H) in relation to the integrated area of all peaks related to the polymer backbone and methyl groups in the range between about 0.6-2.4 ppm. For the sake of illustration, FIG. 2 shows the $^1$H-NMR spectrum of the copolymer of Example 4-1 in deuterated methanol. The indicated integrated peak areas are reported relative to the integrated area of the peak at about 3.8 ppm (integrated peak area: 1.0). The peaks in the region of 0.6-2.4 ppm are attributed to the protons of the —CH$_2$—C(CH$_3$)— backbone moiety of HEMA and the protons of the —CH$_2$—CH— backbone moiety as well as the protons of the two methyl groups of NIPAM. Hence, the integrated peak area in the region of 0.6-2.4 ppm originates from 5 protons of HEMA and 9 protons of NIPAM. From the peak at 3.8 ppm a value of 0.5 follows for the integrated peak area per proton of a HEMA structural unit. Thus a value of 5×0.50=2.5 of the integrated peak area in the region of 0.6-2.4 ppm can be attributed to the five protons of the —CH$_2$—C(CH$_3$)— backbone moiety of HEMA. The remaining value of 11.6−2.50=9.1 may then be attributed to the above-mentioned nine protons of the NIPAM units. Consequently an integrated peak area of 9.1/9=1.01 is deduced per proton of a NIPAM unit. Therefore from the relative integrated peak area per proton for both types of considered structural units, the molar fraction of NIPAM-derived structural units in the copolymer can be deduced as 1.01/(0.50+1.01)=67 mol % and the molar fraction of HEMA-derived structural units in the copolymer follows as 0.50/(0.50+1.01)=33 mol %.

d) Poly(NIPAM-co-AA): The molar fraction of the structural units derived from NIPAM or AA, respectively, in the polymer backbone was calculated from the integrated area of the peak at about 4.0 ppm attributed to the proton of the N—CH moiety of the NIPAM units (1 H) in proportion to the integrated area of all peaks related to the polymer backbone and methyl groups in the range between about 0.6-2.5 ppm (3 H due to AA backbone, 3 H due to NIPAM backbone and 6 H due to methyl groups of NIPAM) analogously to the procedure discussed above for poly(NIPAM-co-HEMA).

e) Poly(DEA-DMA): For quantification of monomer incorporation for poly(DEA-co-DMA), the integrals from all of the $^{13}$C peaks were used in calculating the results (12-16 ppm, CH$_3$ on DEA; 32-39.5 ppm, polymer backbone for both monomers and CH$_3$ of DMA; 39.5-43.5 ppm, NCH$_2$ of DEA; 174 ppm, CO of DEA; 175 ppm, CO of DMA). A relative number of moles of DEA was determined by calculating the average of half the integral of the peaks at 12-16 ppm (2 CH$_3$ groups), half the integral of the peaks at 39.5-43.5 ppm (2CH$_2$ groups), and the integral at 174 ppm (1 CO group). A relative number of moles of DMA was determined by calculating the average of the integral at 175 ppm (1 CO group) and one quarter of the difference between the sum of integrals of peaks at 32-39.5 ppm and twice the relative number of moles of DEA calculated as described above. The mole fraction of each monomer was calculated by dividing the relative number of moles of each respective monomer by the sum of relative number of moles of both monomers.

The thus obtained values for the molar fraction of the constituting structural units derived from the different monomers used in the preparation of the polymers are included in Tables 1-5.

B) Characterization by Size Exclusion Chromatography (SEC)

The absolute number average molecular weight ($M_n$) and the polydispersity index (PDI) were determined for the prepared polymers by size exclusion chromatography (SEC).

In the case of the polymers of Examples 1-1 to 1-24, the polymers of Examples 2-1 to 2-5, the polymers of Examples 4-1 to 4-2 and the polymers of Examples 5-1 to 5-5, SEC was conducted on an Agilent 1260 Infinity high performance liquid chromatography system equipped with one Waters Styragel guard column and three Waters Styragel columns (HR6, HR4, and HR1) with pore sizes suitable for materials with effective molecular weights from 100 to 10,000,000 g/mol. The SEC signals used for analysis included an Agilent 1260 Infinity Variable Wavelength Detector set at a monitoring wavelength of 254 nm (80 Hz data collection frequency), a Wyatt Dawn Heleos II multiangle laser scattering (MALS) detector operated at a laser wavelength of 663.6 nm (18 angles from 10° to 160°) and a Wyatt Optilab T-rEX refractive index detector operated at a wavelength of 658 nm. About 6-7 mg of the respective polymer were dissolved in 1 mL THF and filtered through a 0.2 µm membrane filter. The thus obtained analyte was introduced to the chromatography system and eluted with tetrahydrofuran at a flow rate of 1.0 mL/min, wherein the columns were maintained at a temperature of 25° C. The dn/dc values for each of the polymers were determined offline with the Optilab T-rEX refractometer and were used to calculate the absolute $M_n$ and PDI using ASTRA® 6 software.

In case of the polymers of Examples 3-1 to 3-6, SEC was conducted on an Agilent 1260 high performance liquid chromatography system equipped with Eprogen columns (CATSEC1000 (7 µm, 50×4.6 mm), CATSEC100 (5 µm, 250×4.6 mm), CATSEC300 (5 µm, 250×4.6 mm) and CATSEC1000 (7 µm, 250×4.6 mm)) which were held at a temperature of 30° C. The SEC signals used for analysis included a Wyatt Heleos II light scattering detector operated at a wavelength of 662 nm and an Optilab rEX refractometer operated at a wavelength of 658 nm. About 6-7 mg of the respective polymer were dissolved in 1 mL 0.1 M solution of Na$_2$SO$_4$ in aqueous acetic acid (1.0% v/v) and filtered through a 0.2 µm membrane filter. The thus obtained analyte was introduced to the chromatography system and eluted with 0.1 M solution of Na$_2$SO$_4$ in aqueous acetic acid (1% v/v) at a flow rate of 0.4 mL/min. The dn/dc values for each of the polymers were determined offline with the Optilab rEX refractometer and were used to calculate the absolute $M_n$ using ASTRA® 5 software.

The obtained values for $M_n$ and the polydispersity index (PDI=$M_w/M_n$) are set forth in Tables 1-5.

C) Determination of LCST

For some of the prepared polymers the lower critical solution temperature (LCST) as the temperature around which a reversible transition from a molecularly dissolved or optically clear dispersion of colloidal aggregates/micelles (below the LCST) to a turbid dispersion of larger particles (above the LCST) occurred was determined as follows:

In the case of the polymers of Examples 1-17 to 1-20, 1-22, and 2-1 to 2-5, the LCST measurement was conducted in a CARY 100 Bio UV-Vis spectrophotometer equipped with a heating system and a temperature control unit. A 1.0 wt. % solution of the respective polymer in water and/or in phosphate buffered saline with 0.5 wt. % fasted state simulated intestinal fluid (FaSSIF) of pH 6.5 was provided. The phosphate buffered saline solution of 82 mM NaCl, 20 mM $Na_2HPO_4.7H_2O$, 47 mM $KH_2PO_4$ was prepared by dissolving 0.96 g of NaCl, 1.07 g of sodium phosphate dibasic heptahydrate ($Na_2HPO_4.7H_2O$), and 1.28 g potassium phosphate monobasic ($KH_2PO_4$) in 200 ml of Millipore water. For each LCST measurement in PBS, 9 mg of SIF powder was added to 1.8 mL of above prepared solution (pH 6.5) to obtain 0.5 wt % phosphate buffered saline with 0.5 wt % fasted state simulated intestinal fluid. A cell (Semi-Micro Rectangular Cells, path length 10 mm) was filled with the respective polymer solution, inserted in the spectrophotometer, and the temperature of the solution was increased from 25° C. to 70° C. at a heating rate of 0.2 K/min Herein, the transmittance of the solution at a wavelength of 450 nm was measured. The LCST was determined as the inflection point of a least square fit to the measured data in a transmittance [%] vs. temperature plot.

In the case of the polymers of Examples 1-1 to 1-16, 3-1 to 3-6, and 5-1 to 5-5, the LCST was measured for 1.0 wt % solutions of the respective polymer in deionized water and/or in phosphate buffered saline (PBS, pH 6.5) with 0.5 wt % fasted simulated intestinal fluid powder (Biorelevant.com, UK). PBS was prepared as a solution of 82 mM sodium chloride (Fisher, ≥99.0%), 20 mM sodium phosphate dibasic heptahydrate (Fisher, 98%), and 47 mM potassium phosphate monobasic (J. T. Baker, ≥99.0%). For each measurement a 0.7 mL aliquot of the respective polymer solution was transferred into a 1.0 mL glass vial. The filled vial was installed on an in-house built system for temperature scanning turbidity measurements comprising a heated stage with 51 sample vials mounted in a verticle panel on an oscillating stage for agitation, a QImaging QICAM Fast 1394 camera and internally developed software for analyzing captured images. A flat uniform white light emitting panel was positioned behind the vial-holding panel. A region of interest within a circular optical window was defined in the software for each vial. The solution was heated from 24° C. to 97° C. at a rate of 0.5 K/min. Herein the camera recorded an image at an interval of 1 min. The LCST was determined as the cloud temperature, i.e. the temperature where the average optical transmittance dropped below 95% of the optical transmittance of the fully dissolved solution within the region of interest at 24° C.

The thus obtained LCST values are included in Tables 1, 2, 3 and 5.

Polymer Solubility Test

The solubility of the polymers of Examples 1-12 and 1-15 in aqueous media of different pH value was tested. For each test the respective polymer was added to McIlvaine buffers of pH 4.0, 4.4, 5.0, 5.4, and 6.0 in an amount corresponding to 1 wt. %, based on the total amount of polymer and solvent, in a vial. The vial was stirred for 30 min and then examined for visual clarity. Each Example was visibly clear, indicating complete solubility within this range of pH conditions.

Supersaturation Test

The capabilities of the prepared polymers for inhibiting precipitation or crystallization of drugs from supersaturated solutions (i.e. "supersaturation maintenance") were investigated by the following high-throughput method: For each investigated polymer an aqueous solution of the polymer in a phosphate buffer saline (82 mM sodium chloride, 20 mM sodium phosphate dibasic, 47 mM potassium phosphate monobasic, 0.5 wt. % FaSSIF, adjusted to pH 6.5 with NaOH) having a concentration of 1 wt. % of the respective polymer, based on the total weight of the solution was prepared. These solutions were each robotically delivered in an amount of 912 μL into individual vials arranged on an aluminum 8×12 well array using an Evo 2000 platform. Subsequently, 48 μL of a solution of a drug (Phenytoin or Nilutamide) in methanol having a concentration of 20 g drug per liter of methanol were delivered to each polymer solution. Drug solution was delivered such that each respective experimental combination of drug and polymer was run in quadruplicate. The mixtures were agitated by using the Evo 2000 pipettes to conduct three cycles of aspiration and dispensing. The samples were placed in an isothermal aluminum sample holder at 37° C. At certain points of time after addition of the drug to the polymer solutions (30 min, 90 min and 180 min) the samples were subjected to centrifugation at 2,080×g for 4 min and an aliquot of 30 μL was taken from the supernatant for each sample and diluted with 150 μL methanol. The solubilized drug concentration in each taken aliquot was determined by reverse phase high-performance liquid chromatography (HPLC) analysis. For this purpose 2 μL of the respective diluted taken aliquot were injected to an Agilent 1100 HPLC system equipped with a reversed-phase XDB-C8 column (Eclipse, 4.6×150 mm, 5.0 μm from Agilent, USA). The system was operated at a temperature of 30° C. using a mixture of acetonitrile and water (50:50 v/v for Nilutamide and 40:60 v:v for Phenytoin) as mobile phase at a flow rate of 2.0 mL/min. The effluent from the column was detected by a diode array detector (1100 DAD from Agilent, USA) at a wavelength of 220 nm. The drug concentration was determined from the measured elution profile by using a linear calibration curve for the respective drug, which was generated by determining the least squares fit of a straight line that described the relation between the concentration of four solutions of known concentrations (about 250, 500, 750, and 1000 mg/L) and the respective peak area integral after injection of 2 μL of each drug in methanol. For comparative reasons the afore-mentioned test procedure was performed analogously with the drug added to a) the phosphate buffer saline without any polymer dissolved therein, or b) the phosphate buffer saline with 1 wt. % of a commercial solubilizer (Soluplus from BASF or HPMCAS AFFINISOL™ 912 G from The Dow Chemical Company, respectively). The measured drug concentrations, which are reported as the average value of quadruplicate runs, are summarized and discussed in the following. It should be noted that due to minor variations associated with delivery of small volumes (i.e. 48 μL drug solution) robotically that the target maximum drug concentration of 1000 μg/mL was sometimes exceeded.

TABLE 6

Concentration of solubilized Phenytoin in 1 wt. % solutions of different prepared NIPAM-co-DMA polymers and of commercial solubilizers (HPMCAS, BASF Soluplus) in phosphate buffered saline with FaSSIF (pH 6.5), as well as in neat phosphate buffered saline with FaSSIF (pH 6.5) as determined by above-discussed supersaturation maintenance test at different times after drug addition.

| Polymer | mol % NIPAM | mol % DMA | $M_n$ [g/mol] | c(30 min) [mg/L] | c(90 min) [mg/L] | c(180 min) [mg/L] |
|---|---|---|---|---|---|---|
| Ex. 1-1 | 66 | 34 | 10,950 | 1,208 | 1,024 | 1,104 |
| Ex. 1-2 | 66 | 34 | 20,000 | 1,010 | 760 | 853 |
| Ex. 1-3 | 67 | 33 | 30,000 | 992 | 794 | 876 |
| Ex. 1-4 | 65 | 35 | 42,000 | 1,066 | 758 | 936 |
| Ex. 1-5 | 66 | 34 | 69,000 | 942 | 759 | 823 |
| Ex. 1-6 | 68 | 32 | 54,500 | 962 | 649 | 875 |
| Ex. 1-7 | 8 | 92 | 20,600 | 156 | 137 | 145 |
| Ex. 1-8 | 19 | 81 | 17,900 | 183 | 173 | 184 |
| Ex. 1-9 | 30 | 70 | n/a | 301 | 266 | 265 |
| Ex. 1-10 | 42 | 58 | 19,600 | 392 | 281 | 255 |
| Ex. 1-11 | 54 | 46 | 14,300 | 895 | 343 | 300 |
| Ex. 1-12 | 63 | 37 | 17,800 | 1,050 | 1,003 | 1,033 |
| Ex. 1-13 | 63 | 37 | 18,900 | 1,146 | 654 | 664 |
| Ex. 1-14 | 73 | 27 | 17,700 | 848 | 685 | 743 |
| Ex. 1-15 | 76 | 24 | 11,300 | 479 | 455 | 409 |
| Ex. 1-16 | 90 | 10 | n/a | 413 | 379 | 407 |
| BASF Soluplus (Comp.) | — | — | n/a | 404 | 304 | 336 |
| HPMCAS (Comp.) | — | — | n/a | 352 | 295 | 296 |
| None (Comp.) | — | — | — | 75 | 70 | 73 | n/a: not available

As can be seen from Table 6, the investigated NIPAM-co-DMA polymers increase the amount of solubilized Phenytoin significantly (factor of 2 to 10 or more relative to Phenytoin as such) similarly to BASF Soluplus and HPMCAS used as benchmark solubilizers. From the series of Examples 1-7 to 1-16 (systematic variation of molar composition at comparable $M_n$: 16,000±5,000) it can be seen that particularly effective solubilization (enhanced solubilization compared to BASF Soluplus or HPMCAS) is achieved for those copolymers that comprise more than 50 mol % structural units derived from NIPAM with the most efficient solubilization observed for copolymers comprising about 60 to 75 mol % structural units derived from NIPAM (cf. Examples 1-2 and 1-12 to 1-14). These solubilization capabilities of the NIPAM-co-DMA polymers are obtainable in a wide range of molecular weight as illustrated by Examples 1-1 to 1-6, wherein $M_n$ was systematically varied from about 10,000 to about 70,000 g/mol for copolymers comprising about 66±2 mol % NIPAM-derived structural units. The supersaturated state may basically be maintained by the NIPAM-co-DMA polymers over the entire investigated period of 180 min.

As evidenced by Table 7 also Nilutamide is more efficiently solubilized by NIPAM-co-DMA polymers according to the present invention than by the benchmark BASF Soluplus. In the above-indicated preferred compositional range of about 60 to 75 mol % structural units derived from NIPAM the full provided amount of Nilutamide (corresponding to 1,000 mg/L) is solubilized in the PBS-FaSSIF buffer solution and the supersaturated state is maintained over the entire investigated period of 180 min.

TABLE 7

Concentration of solubilized Nilutamide in 1 wt. % solutions of different prepared NIPAM-co-DMA polymers and of commercial solubilizer (BASF Soluplus) in phosphate buffered saline with FaSSIF (pH 6.5), as well as in neat phosphate buffered saline with FaSSIF (pH 6.5) as determined by above-discussed supersaturation test at different times after drug addition.

| Polymer | mol % NIPAM | mol % DMA | Mn [g/mol] | c(30 min) [mg/L] | c(90 min) [mg/L] | c(180 min) [mg/L] |
|---|---|---|---|---|---|---|
| Ex. 1-12 | 63 | 37 | 17.800 | 1,135 | 1,104 | 1,135 |
| Ex. 1-13 | 63 | 37 | 18.900 | 1,102 | 1,106 | 1,136 |
| Ex. 1-2 | 66 | 34 | 20.000 | 1,135 | 1,104 | 1,135 |
| Ex. 1-14 | 73 | 27 | 17.700 | 1,126 | 1,060 | 1,154 |
| Ex. 1-15 | 76 | 24 | 11.300 | 828 | 833 | 848 |
| BASF Soluplus (Comp.) | — | — | — | 601 | 612 | 610 |
| None (Comp.) | — | — | — | 473 | 364 | 308 |

Also NIPAM-co-AA polymers have a solubilizing effect on Phenytoin (cf. Table 8). As the comparison of Examples 3-1 to 3-6 indicates the solubilization efficiency increases systematically with the molar fraction of structural units derived from NIPAM in the investigated compositional range (27 mol %-73 mol % NIPAM-derived structural units). At least the copolymer of Example 3-6 achieves a clearly superior solubilization capacity compared to BASF Soluplus and HPMCAS. This finding has also been verified for Nilutamide (not shown). Generally, the NIPAM-co-DMA polymers seem to be somewhat more effective in stabilizing the supersaturated state than the corresponding NIPAM-co-AA polymers, which exhibit some decrease of the concentration of solubilized Phenytoin with time.

TABLE 8

Concentration of solubilized Phenytoin in 1 wt. % solutions of different prepared NIPAM-co-AA polymers in phosphate buffered saline with FaSSIF (pH 6.5) as determined by above-discussed supersaturation test at different times after drug addition.

| Polymer | mol % NIPAM | mol % AA | Mn [g/mol] | c(30 min) [mg/L] | c(90 min) [mg/L] | c(180 min) [mg/L] |
|---|---|---|---|---|---|---|
| Ex. 3-1 | 27 | 73 | 17,500 | 121 | 147 | 105 |
| Ex. 3-2 | 36 | 64 | 23,800 | 150 | 159 | 126 |
| Ex. 3-3 | 45 | 55 | 18,500 | 232 | 216 | 182 |
| Ex. 3-4 | 57 | 43 | 23,400 | 315 | 262 | 183 |
| Ex. 3-5 | 65 | 35 | 19,900 | 344 | 273 | 233 |
| Ex. 3-6 | 73 | 27 | 21,700 | 966 | 797 | 519 |

In the above-indicated preferred compositional range of 60-75 mol % NIPAM-derived structural units also the solubilizing capabilities of NIPAM-co-HEMA-polymers have been investigated. As to be seen from Tables 9 and 10 in combination with Table 6, the NIPAM-co-HEMA-polymers achieve better solubilization than the tested benchmark solubilizers for Phenytoin as well as for Nilutamide. The concentration of solubilized drug remains stable within measurement accuracy over the investigated period of 180 min.

TABLE 9

Concentration of solubilized Phenytoin in 1 wt. % solutions of different prepared NIPAM-co-HEMA polymers in phosphate buffered saline with FaSSIF (pH 6.5) as determined by above-discussed supersaturation test at different times after drug addition.

| Polymer | mol % NIPAM | mol % HEMA | Mn [g/mol] | c(30 min) [mg/L] | c(90 min) [mg/L] | c(180 min) [mg/L] |
|---|---|---|---|---|---|---|
| Ex. 4-1 | 67 | 33 | 25,200 | 378 | 405 | 356 |
| Ex. 4-2 | 78 | 22 | 26,300 | 394 | 432 | 381 |

TABLE 10

Concentration of solubilized Nilutamide in 1 wt. % solutions of different prepared NIPAM-co-HEMA polymers in phosphate buffered saline with FaSSIF (pH 6.5) as determined by above-discussed supersaturation test at different times after drug addition.

| Polymer | mol % NIPAM | mol % HEMA | Mn [g/mol] | c(30 min) [mg/L] | c(90 min) [mg/L] | c(180 min) [mg/L] |
|---|---|---|---|---|---|---|
| Ex. 4-1 | 67 | 33 | 25,200 | 862 | 859 | 863 |
| Ex. 4-2 | 78 | 22 | 26,300 | 832 | 806 | 835 |

The DEA-co-DMA polymers were found to behave similarly to the NIPAM-co-DMA polymers and yield at least for compositions comprising 50 mol % or more of structural units derived from DEA comparable or even enhanced solubilization of Phenytoin relative to BASF Soluplus and HPMCAS (cf. Table 11). This has also been verified for Nilutamide (not shown).

TABLE 11

Concentration of solubilized Phenytoin in 1 wt. % solutions of different prepared DEA-co-DMA polymers in phosphate buffered saline with FaSSIF (pH 6.5) as determined by above-discussed supersaturation test at different times after drug addition.

| Polymer | mol % DEA | mol % DMA | Mn [g/mol] | c(30 min) [mg/L] | c(90 min) [mg/L] | c(180 min) [mg/L] |
|---|---|---|---|---|---|---|
| Ex. 5-1 | 20 | 80 | 22,700 | 172 | 197 | 137 |
| Ex. 5-2 | 40 | 60 | 21,700 | 319 | 322 | 223 |
| Ex. 5-3 | 50 | 50 | 23,600 | 595 | 413 | 257 |
| Ex. 5-4 | 65 | 35 | 15,400 | 646 | 667 | 591 |
| Ex. 5-5 | 81 | 19 | 28,600 | 348 | 359 | 295 |

Preparation of Solid Polymer-Drug Mixtures

Solid mixtures of the polymers according to Table 1, of the polymers according to Table 2 and of HPMCAS AFFINISOL™ 912 G from The Dow Chemical Company as benchmark excipient, respectively, with a poorly water soluble drug (Probucol or Phenytoin) were prepared by spray drying using a Bend Research Mini Spray Dryer (Bend, Oreg.): In each case a solution of the respective polymer and drug in either acetone or an acetone-methanol mixture (1:1, v/v) having a total concentration of polymer and drug of 2 wt. %, based on the total weight of the solution, was prepared by adding the solid components into the solvent and rigorous stirring until a homogeneous solution had been formed. The amount of drug was selected herein such as to correspond to 10 wt. %, 25 wt. % or 50 wt. %, respectively, of the total weight of polymer and drug. For example, 20 mg of drug were combined with 180 mg of polymer in 9.8 g of solvent to prepare a solution having a 2 wt. % total solute content with a 10 wt. % drug loading. The prepared solution was injected with a 20 mL syringe to the spray dryer with a feed rate of 0.65 ml/min. Nitrogen gas was fed to the spray dryer at a rate of 12.8 standard liter per minute. The inlet temperature of the spray dryer was maintained at 90° C., the outlet temperature was not controlled and ranged from 24-29° C. The solid polymer-drug mixtures were collected at the outlet on a 1.5" Whatman filter paper, removed therefrom with assistance of an antistatic bar and dried in vacuo (10 mTorr) for at least 12 h. The dried solid mixture was stored in a desiccator at 22° C. for further use.

Characterization of the Solid Polymer-Drug Mixtures

Figure 3:
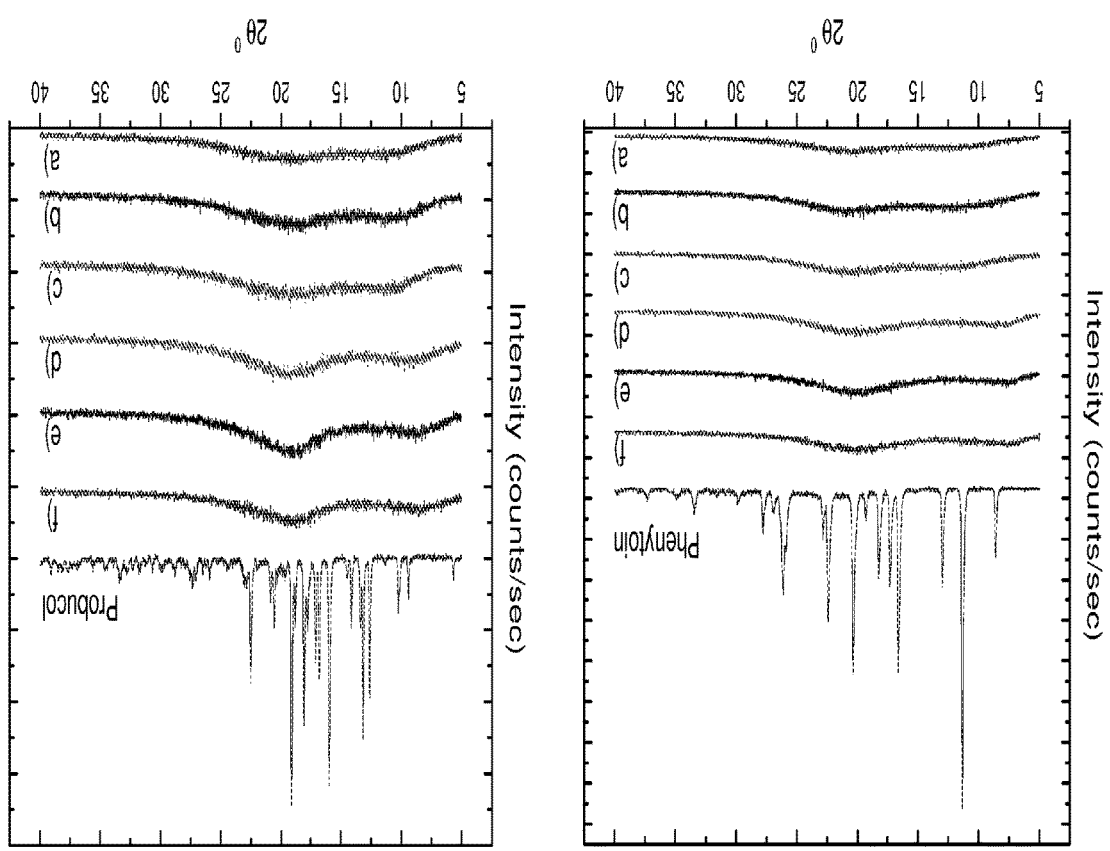
FIG. 3 shows X-ray diffraction patterns of solid mixtures of Phenytoin (left) or Probucol (right) with a) the DMA homopolymer of Example 1-23 (Comparative Example), b) the NIPAM-co-DMA polymer of Example 1-17, c) the NIPAM-co-DMA polymer of Example 1-18, d) the NIPAM-co-DMA polymer of Example 1-19, e) the NIPAM-co-DMA polymer of Example 1-20 or f) the NIPAM homopolymer of Example 1-22 (Comparative Example) with a drug loading of 25 wt. % in comparison to the X-ray diffraction pattern of the respective crystalline pure drug (uppermost curve).

The prepared solid polymer-drug mixtures were analyzed by powder X-ray diffraction. Powder X-ray diffraction experiments were conducted on a Bruker-AXS (Siemens) D5005 Diffractometer with a 2.2 kW sealed Cu ($\lambda$=1.54 Å) source equipped with a scintillation counter detector. Samples (~50 mg) were packed evenly into standard glass holders. Measurements were taken at a voltage of 40 kW and current of 45 mA. Samples were analyzed in the $2\theta$ angle range of 5-40° with a step size of 0.02 and scan step time of 0.5 s. The XRD patterns of the mixtures exhibit merely broad "halo" signals associated to near range order in a glassy state, but no sharp peaks as would be characteristic for crystalline phase(s). FIG. 3 shows exemplarily XRD patterns of solid mixtures of the copolymers of Examples 1-17 to 1-20 and for comparative reasons of the homopolymers of Examples 1-22 and 1-23 with Phenytoin (left) or Probucol (right) at a drug loading of 25 wt. % in comparison to the respective crystalline pure drug. Accordingly, the drug is present in the prepared solid mixtures in amorphous form. The prepared NIPAM and/or DMA-based polymers stabilize the amorphous form of the drug against crystallization in the solid mixtures.

Figure 4:
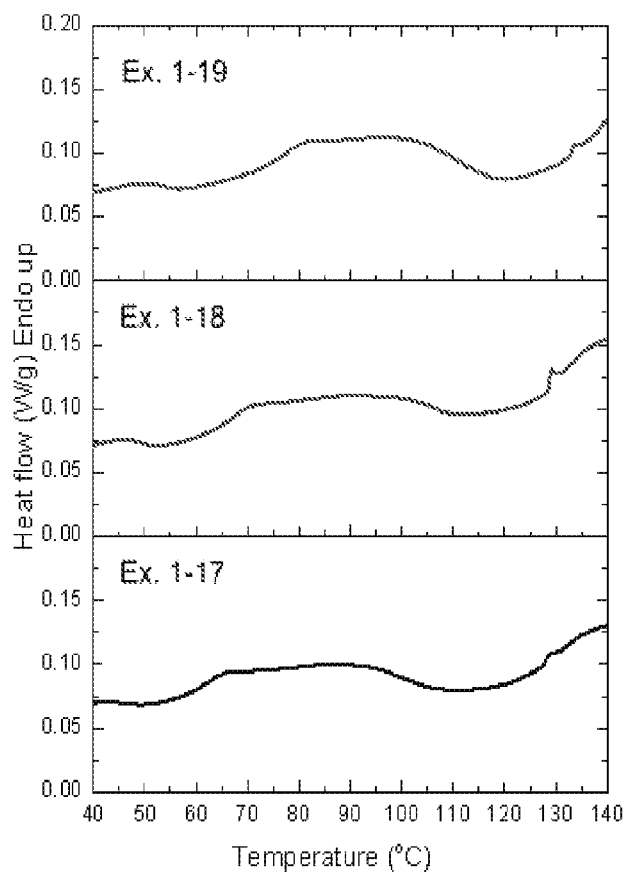
FIG. 4 shows DSC curves for solid mixtures of Phenytoin with different polymers (bottom: NIPAM-co-DMA polymer of Example 1-17, center: NIPAM-co-DMA polymer of Example 1-18, top: NIPAM-co-DMA polymer of Example 1-19) having a drug loading of 25 wt. %.

Furthermore, differential scanning calorimetry measurements were conducted for the prepared solid polymer-drug mixtures using a TA Instruments Discovery DSC. All samples (~5-10 mg) were hermetically crimped in T-zero aluminum pans. The measurements were run in a temperature range from 22° to 180° C. applying a heating rate of 2.5 K/min. TA TRIOS software (Version 2.2) was used to analyze the thermal transitions. The glass transition temperature of each mixture was determined using the reversing thermogram in MDSC during the first heating step. FIG. 4 shows exemplarily DSC curves obtained for the solid mixtures of the copolymers of Examples 1-17 to 1-19 with Phenytoin at a drug loading of 25 wt. %. The DSC curves each exhibit a glass transition, wherein the glass transition temperature increases with increasing molar content of NIPAM-derived structural units in the polymer from about 62° C. (Example 1-17) over about 66° C. (Example 1-18) to about 76° C. (Example 1-19), which is opposite to the trend observed for the copolymers as such (decrease of $T_g$ with increasing molar content of NIPAM). The observed opposite behavior in mixtures with Phenytoin is believed to be indicative of a strong interaction between the drug with NIPAM-derived structural units of the copolymers such as by hydrogen bonding. The presence of a single glass transition temperature for the mixtures indicates the formation of a homogeneous polymer-drug mixture, i.e. a solid solution of the drug in the copolymer. The DSC curves moreover show a crystallization peak between about 95° C. and 130° C. confirming the presence of the drug in amorphous form in the prepared mixtures. Similar results were obtained by thermal analysis for a 10 wt. % drug loading level.

Dissolution Characteristics of the Solid Polymer-Drug Mixtures

The dissolution characteristics of the prepared solid polymer-drug mixtures in aqueous medium were investigated as follows: In each case an amount of the respective solid polymer-drug mixture was carefully weighed into a 2.0 mL plastic conical microcentrifuge tube. Phosphate buffer saline (PBS, 82 mM NaCl, 20 mM $Na_2HPO_4.7H_2O$, 47 mM $KH_2PO_4$ prepared by dissolving 0.96 g of NaCl, 1.07 g of sodium phosphate dibasic heptahydrate ($Na_2HPO_4.7H_2O$), and 1.28 g potassium phosphate monobasic ($KH_2PO_4$) in 200 ml of Millipore water, then adjusted to pH 6.5 with NaOH) with 0.5 wt. % FaSSIF powder (Biorelevant, UK), held at a temperature of 37° C., was added into the microcentrifuge tube in an amount to achieve a final drug concentration of 1,000 mg/L, if the entire amount of drug of the solid polymer-drug mixture weighed into the tube were dissolved. The amount of the solid polymer-drug mixture was chosen such as to yield in total a volume of sample liquid of about 1.8 mL. For instance, in case of solid polymer-drug mixtures with a 25 wt. % drug loading, 7.2 mg of the solid polymer-drug mixture consisting of 1.8 mg drug and 5.4 mg polymer were carefully weighed into the microcentrifuge tube and 1.8 mL of the PBS-FaSSIF solution added thereto. After addition of the PBS-FaSSIF solution the sample was vortexed (Scientific Industries Vortex Genie 2 equipped with a SI-V524 Vertical Microtube Holder) for 30 s and incubated in an isothermal aluminum heating block (VWR Digital Heatblock) at 37° C. At certain points of time after addition of the PBS-FaSSIF solution to the polymer solution (4, 10, 20, 40, 90, 180 and 360 min) the samples were subjected to centrifugation (Eppendorf Centrifuge 5415R or Beckman Coulter Microfuge 16) at 16,000×g for 1 min and an aliquot of 50 µL was taken from the supernatant and diluted with 250 µL methanol. After each taking of an aliquot the remaining sample was vortexed again for 30 s and held at 37° C. until the next aliquot was to be taken. The solubilized drug concentration in each taken aliquot was determined by reverse phase high-performance liquid chromatography (HPLC) analysis. For this purpose 10 µL of the respective diluted taken aliquot were injected to a HPLC system equipped with a reversed-phase EC-C18 column (Poroshell 120, 4.6×50 mm, 2.7 µm from Agilent, USA). The system was operated at a temperature of 30° C. using a mixture of acetonitrile and water (96:4 v/v) as mobile phase at a flow rate of 1.0 ml/min. The effluent from the column was detected by a UV detector (1260 Infinity Multiple Wavelength Detector from Agilent, USA) at a wavelength of 241 nm. The drug concentration was determined from the measured elution profile by using a calibration curve for the respective drug. The measured dissolution profiles for exemplary solid mixtures of several NIPAM-co-DMA polymers with Phenytoin at a 25 wt. % drug loading are presented in FIGS. 5 and 6. Additionally, FIG. 7 shows dissolution profiles measured for solid mixtures of the NIPAM-co-VP polymers according to Table 2 with Phenytoin at a 25 wt. % drug loading. For comparative reasons the dissolution profile of the respective mixture with HPMCAS as excipient is included in these plots. As a measure of the solubilization efficacy the area under the curve in the concentration [mg/L] versus time [min] plots from 0 to 360 min ($AUC_{360\ min}$) was calculated using the trapezoidal rule.

Figure 5:
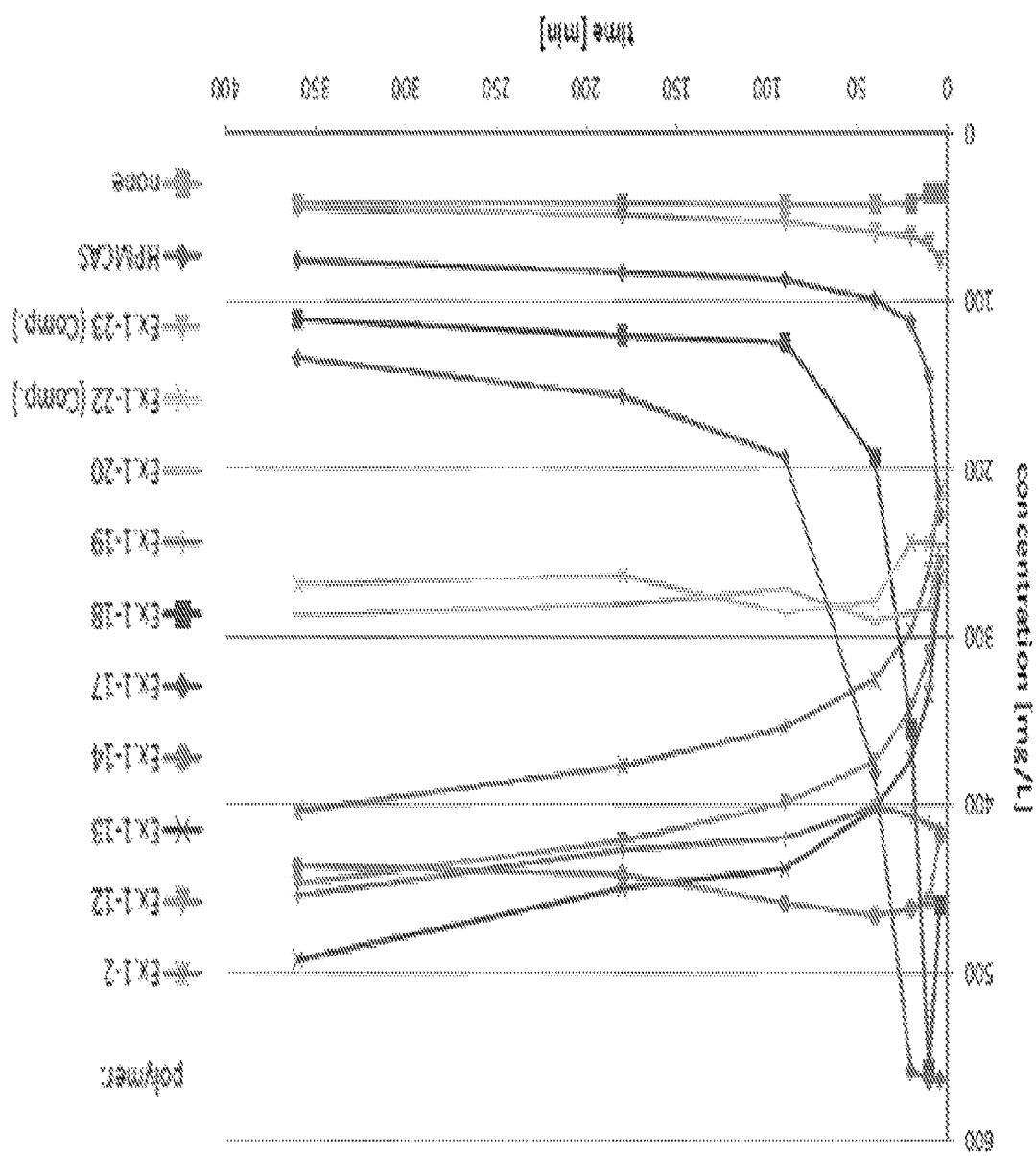
FIG. 5 shows dissolution profiles (solubilised drug concentration versus time) for solid mixtures of Phenytoin with different polymers (curves in their order from top to bottom at t=360 min: a) NIPAM-co-DMA polymer of Example 1-13, b) NIPAM-co-DMA polymer of Example 1-19, c) NIPAM-co-DMA polymer of Example 1-12, d) NIPAM-co-DMA polymer of Example 1-14, e) NIPAM-co-DMA polymer of Example 1-2, f) NIPAM-co-DMA polymer of Example 1-20, g) NIPAM homopolymer of Example 1-22 (Comp. Ex.), h) HPMCAS (Comp. Ex.), i) NIPAM-co-DMA polymer of Example 1-18, j) NIPAM-co-DMA polymer of Example 1-17, l) DMA homopolymer of Example 1-23 (Comp. Ex.)) having a drug loading of 25 wt. % in aqueous PBS-FaSSIF buffer (pH 6.5) compared to the dissolution of neat Phenytoin (bottom curve).

FIG. 5 shows that solid mixtures containing the NIPAM-co-DMA polymer—similarly to mixtures with the homopolymer of NIPAM (Example 1-22) or HPMCAS as polymer—dissolve rapidly and provide within the first 4 min solubilized drug concentrations well above 200 mg/L, partly even above 500 mg/L, which is considerably higher than the about 50 mg/L reached in case of dissolution of Phenytoin as such. In contrast thereto, the homopolymer of DMA (Example 1-23) leads only to slightly increased solubilized drug concentrations compared to the dissolution of the neat drug. In case of the copolymers, which comprise predominantly structural units derived from DMA (Examples 1-17 and 1-18) the solubilized drug concentration decreases in the following continuously to values below 200 mg/L similarly to the behavior observed for the HPMCAS sample, i.e. the initial highly supersaturated state is not retained over an extended period of time. On the other hand the solid mixtures comprising polymers that contain more than 50 mol % structural units derived from NIPAM exhibit different dissolution profiles, wherein the solubilized drug concentration further increases with progressing time approaching limit values towards sufficiently long periods of time. Herein, NIPAM-co-DMA polymers in the compositional range of about 60 to 75 mol % structural units derived from NIPAM (Examples 1-2, 1-12, 1-13, 1-14 and 1-19) are the most efficient solubilizers achieving $AUC_{360\ min}$ values above $1.0 \times 10^5$ mg·min/L and solubilized drug concentrations after 360 min above 400 mg/L (HPMCAS: $AUC_{360\ min}$ of $6.2 \times 10^4$ mg·min/L, $c_{360\ min} \approx 130$ mg/L). For higher content of structural units derived from NIPAM in the copolymer, somewhat lower limit values of the solubilized drug concentration such as about 290 mg/L (t=360 min) in case of Example 1-20 are attained. The NIPAM homopolymer reaches about 270 mg/L (t=360 min), however, its usability as solubilizer is considered limited in many biological applications since the LCST in the relevant aqueous media may be below or close to the temperature(s) encountered in the respective application such as the body temperature of human or animal beings.

Figure 6:
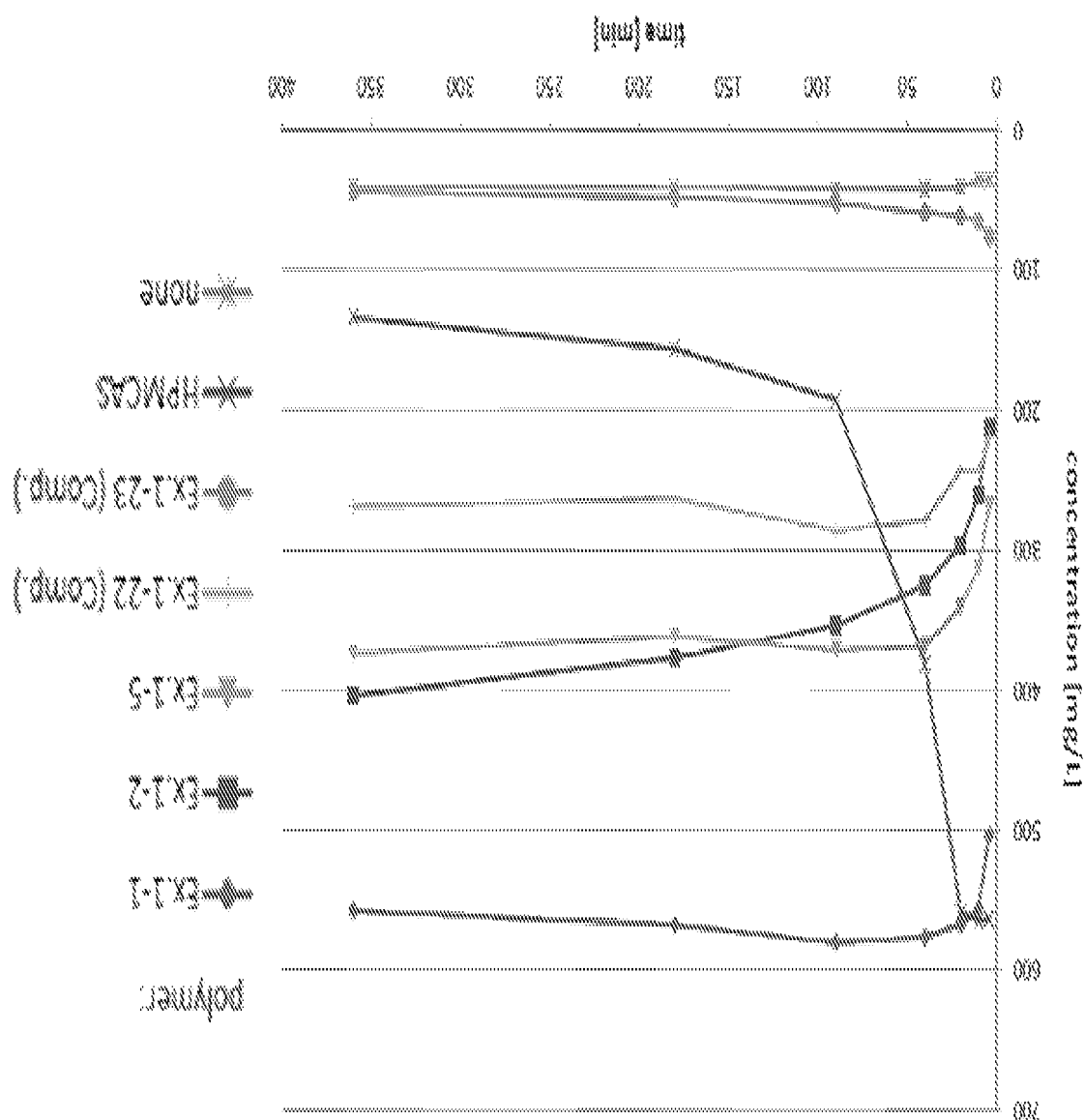
FIG. 6 shows dissolution profiles (solubilised drug concentration versus time) for solid mixtures of Phenytoin with different polymers (curves in their order from top to bottom at t=360 min: a) NIPAM-co-DMA polymer of Example 1-1, b) NIPAM-co-DMA polymer of Example 1-2, c) NIPAM-co-DMA polymer of Example 1-5, d) NIPAM homopolymer of Example 1-22 (Comp. Ex.), e) HPMCAS (Comp. Ex.), f) DMA homopolymer of Example 1-23 (Comp. Ex.)) having a drug loading of 25 wt. % in aqueous PBS-FaSSIF buffer (pH 6.5) compared to the dissolution of neat Phenytoin (bottom curve).
Figure 7:
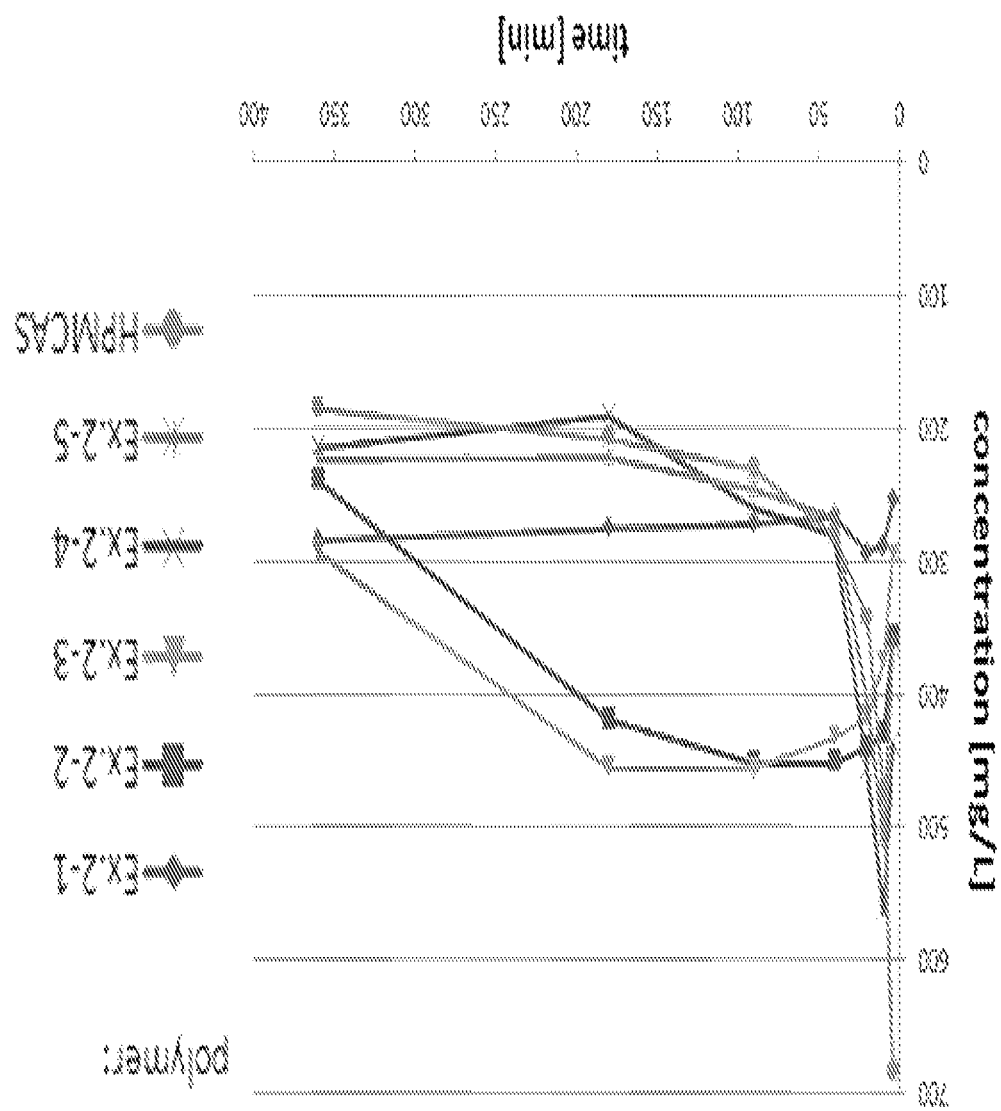
FIG. 7 shows dissolution profiles (solubilised drug concentration versus time) for solid mixtures of Phenytoin with each a different NIPAM-co-VP polymer (Examples 2-1 to 2-5) or with HPMCAS (Comp. Ex.) having a drug loading of 25 wt. % in aqueous PBS-FaSSIF buffer (pH 6.5).

FIG. 6 illustrates that the afore-mentioned efficient dissolution and solubilization characteristics of solid mixtures of Phenytoin with NIPAM-co-DMA polymers in the preferred compositional range are obtained in a wide molecular weight range as to be seen from the dissolution profiles of the copolymers of Examples 1-1 ($M_n$: 10,950 g/mol), 1-2 ($M_n$: 20,000 g/mol) and 1-5 ($M_n$: 69,000 g/mol), which each comprise about 66 mol % structural units derived from NIPAM.

FIG. 7 shows that solid mixtures of Phenytoin with NIPAM-co-VP polymers likewise enable efficient dissolution and solubilization characteristics at least comparable to analogous solid Phenytoin-HPMCAS mixtures. Herein, the mixtures that contain NIPAM-co-VP polymers, which comprise predominantly structural units derived from VP (Examples 2-4 and 2-5) behave very similar to the mixtures with HPMCAS as excipient, i.e. exhibit an initial burst dissolution achieving concentrations of solubilized drug of more than 500 mg/L within the first few minutes and subsequently a steady decrease of the solubilized drug concentration to values below 250 mg/L after 360 minutes. Those solid mixtures that comprise NIPAM-co-VP polymers, which have about equal proportions of constituting structural units derived from NIPAM and VP, respectively (Example 2-3), or a moderate excess of NIPAM-derived structural units (Example 2-4) show a different dissolution behavior with a steady increase of the solubilized drug concentration within the first about 60 minutes to a maximum of about 450 mg/L. This supersaturated state is substantially maintained at least up to 180 minutes, whereas at longer times the solubilized drug concentration decreases. Nevertheless over the entire investigated period of 360 minutes the mixtures corresponding to Examples 2-3 and 2-4 achieve $AUC_{360\ min}$ values of about 1.4×10⁵ mg·min/L, which demonstrates that they may provide substantially higher integrated amounts of solubilized drug compared to HPMCAS. The mixture that contains the NIPAM-co-VP polymer of Example 2-1 with the highest investigated content of NIPAM-derived structural units (74 mol %) shows moreover an almost constant solubilized drug concentration of about 280 mg/L over the entire observed period of 360 minutes with no indication of a beginning re-precipitation of solubilized drug.

The above-mentioned findings illustrate the capability of the copolymers according to the present invention to not only dissolve a poorly water soluble substance in a rapid and controlled manner from solid mixtures comparable to established prior art solubilizers like HPMCAS, but to also stabilize the solubilized substance more efficiently versus re-precipitation in the aqueous medium and maintain a highly supersaturated state for substantially longer periods of time.

The invention claimed is:

1. A composition comprising a solid mixture comprising
   a) at least one uncrosslinked copolymer having a backbone comprising
      i) a plurality of thermo-responsive structural units derived from one or more than one first monomer, which is an N-alkyl or N,N-dialkyl substituted (alkyl)acrylamide monomer, and
      ii) a plurality of hydrophilic structural units derived from one or more than one second monomer, which is an ethylenically unsaturated monomer, and
   b) at least one poorly water soluble substance having as such a solubility in deionized water of pH 7.0 of 200 mg/L or less at a temperature of 23° C. and an atmospheric pressure of 1 atm,
   wherein the molar ratio of the thermo-responsive structural units i) to the hydrophilic structural units ii) comprised in the copolymer is in a range from 1:1 to 10:1,
   wherein the thermo-responsive structural units i) and hydrophilic structural units ii) are more than 80 mol % based on the total amount of monomer-derived structural units constituting the copolymer,
   wherein the solid mixture is a solid dispersion or solid solution of the at least one poorly water-soluble substance b) in the at least one uncrosslinked copolymer a), and
   wherein the at least one uncrosslinked copolymer a) is non-ionic, soluble in an aqueous medium, and does not have a three-dimensional network structure.

2. The composition of claim 1, wherein the copolymer is a random copolymer and/or is a linear copolymer.

3. The composition of claim 1, wherein the molar ratio of the thermo-responsive structural units i) to the hydrophilic structural units ii) comprised in the copolymer is in a range from 1.2:1 to 5:1.

4. The composition of claim 1, wherein the copolymer comprises from 55 mol % to 80 mol % of the thermo-responsive structural units i) and/or from 20 mol % to 45 mol % of the hydrophilic structural units ii), based on the total amount of monomer-derived structural units constituting the copolymer, wherein the amounts of the thermo-responsive structural units i) and the hydrophilic structural units ii) sum up to 100 mol %.

5. The composition of claim 1, wherein the N-alkyl or N,N-dialkyl substituted (alkyl)acrylamide monomer from which the thermo-responsive structural units i) are derived is selected from the group consisting of N-isopropylacrylamide, N,N-diethylacrylamide, N-tert-butylacrylamide, N-isopropylmethacrylamide, N,N-diethylmethacrylamide, N-tert-butylmethacrylamide and combinations thereof.

6. The composition of claim 1, wherein the ethylenically unsaturated monomer from which the hydrophilic structural units ii) are derived is selected from vinyl-substituted heterocyclic compounds and/or one or more than one compound having a structure

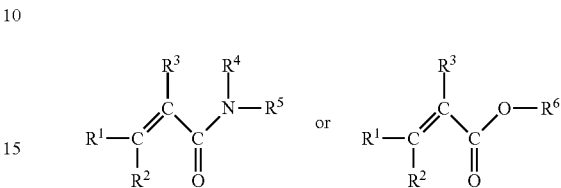

wherein each of $R^1$, $R^2$, $R^3$, $R^4$, $R^5$ and $R^6$ is independently selected from hydrogen and a monovalent organic group having from 1 to 6 carbon atoms, wherein $R^6$ may alternatively also be a moiety derived by esterification from a glycol.

7. The composition according to claim 6, wherein the ethylenically unsaturated monomer from which the hydrophilic structural units ii) are derived is selected from the group consisting of N,N-dimethylacrylamide, acrylamide, 2-hydroxyethyl-methacrylate, 4-vinyl-pyrrolidone and combinations thereof.

8. The composition of claim 1, wherein the copolymer is poly-[(N-isopropylacrylamide)-co-(N,N-dimethylacrylamide)].

9. The composition of claim 1, wherein the copolymer has a number average molecular weight in the range from 3,000 to 400,000 g/mol and/or has a polydispersity index of less than 2.5 as measured each by size exclusion chromatography.

10. The composition according to claim 1, wherein the at least one poorly water soluble substance b) is selected from an active pharmaceutical ingredient, an active personal care agent, a plant protective agent, an insecticide or foodstuff.

11. The composition according to claim 1, wherein the at least one poorly water soluble substance b) is at least partly present in amorphous form.

12. The composition according to claim 1, wherein the composition comprises 60 to 95 wt. % of the at least one copolymer a) and 5 to 40 wt. % of the at least one poorly water soluble substance b), based on the total weight of the composition.

13. The composition according to claim 1 further comprising at least one ingredient selected from the group consisting of fillers, binders, pH regulators, solvents, surfactants, antioxidants, preservative agents, plasticizers, colouring agents, flavouring agents, mineral adjuvants, emollients, lubricants, perfumes and combinations thereof.

14. A solid dosage form comprising the composition according to claim 1.

15. The composition of claim 1, wherein the at least one uncrosslinked copolymer is a binary copolymer.

16. The composition of claim 1, wherein the at least one uncrosslinked copolymer comprise more than 50 mol % structural units derived from N-isopropylacrylamide.

17. The composition of claim 1, wherein the copolymer is a linear copolymer.

* * * * *